United States Patent
Mihashi et al.

(10) Patent No.: US 6,234,978 B1
(45) Date of Patent: May 22, 2001

(54) OPTICAL CHARACTERISTIC MEASURING APPARATUS

(75) Inventors: Toshifumi Mihashi; Yasufumi Fukuma, both of Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 09/023,058

(22) Filed: Feb. 12, 1998

(30) Foreign Application Priority Data

Feb. 12, 1997 (JP) .................................................. 9-042940
May 9, 1997 (JP) .................................................. 9-136214

(51) Int. Cl.[7] .................................................. A61B 5/00
(52) U.S. Cl. .................................................. 600/558
(58) Field of Search .................................. 600/558, 587; 351/212

(56) References Cited

U.S. PATENT DOCUMENTS

| | | | |
|---|---|---|---|
| 4,353,625 | * 10/1982 | Nohda | 351/13 |
| 4,390,255 | * 6/1983 | Nohda et al. | 351/211 |
| 5,062,702 | 11/1991 | Bille | 351/212 |

FOREIGN PATENT DOCUMENTS 4222395   1/1994   (DE) .

OTHER PUBLICATIONS

"Objective Measurement of Wave Aberrations of the Human Eye with the use of a Hartmann–Shack Wave–Front Sensor" by Liang et al.; vol. 11, No. 7/Jul. 1994/J. Opt.Soc.Am.A; p. 1949–1957.

* cited by examiner

Primary Examiner—Max Hindenburg
Assistant Examiner—Pamela L. Wingood
(74) Attorney, Agent, or Firm—Baker Botts L.L.P.

(57) ABSTRACT

The present invention relates to an apparatus for the precision measurement of the optical characteristics of the eye and the shape of the cornea of the eye. An object of the present invention is to provide an optical characteristic measuring apparatus capable measuring the optical characteristics of an irregular astigmatism component. An illuminating optical system illuminates a minute region on the retina of the eye with light rays emitted by an illuminating light source, a reflected light guiding optical system guides reflected light rays reflected from the retina of the eye to a light receiving device, a converting device converts the reflected light rays into at least seventeen light beams, a light receiving device receives the plurality of light beams from the converting device, and an arithmetic unit determines the optical characteristics of the eye and the shape of the cornea on the basis of the inclination of the light rays determined by the light receiving device.

15 Claims, 18 Drawing Sheets

ELLIPSES INDICATE MAXIMUM POWER, MINIMUM POWER, THE DIRECTION OF MAXIMUM POWER AND THE DIRECTION OF MINIMUM POWER

REGULAR ASTIGMATISM

IRREGULAR ASTIGMATISM

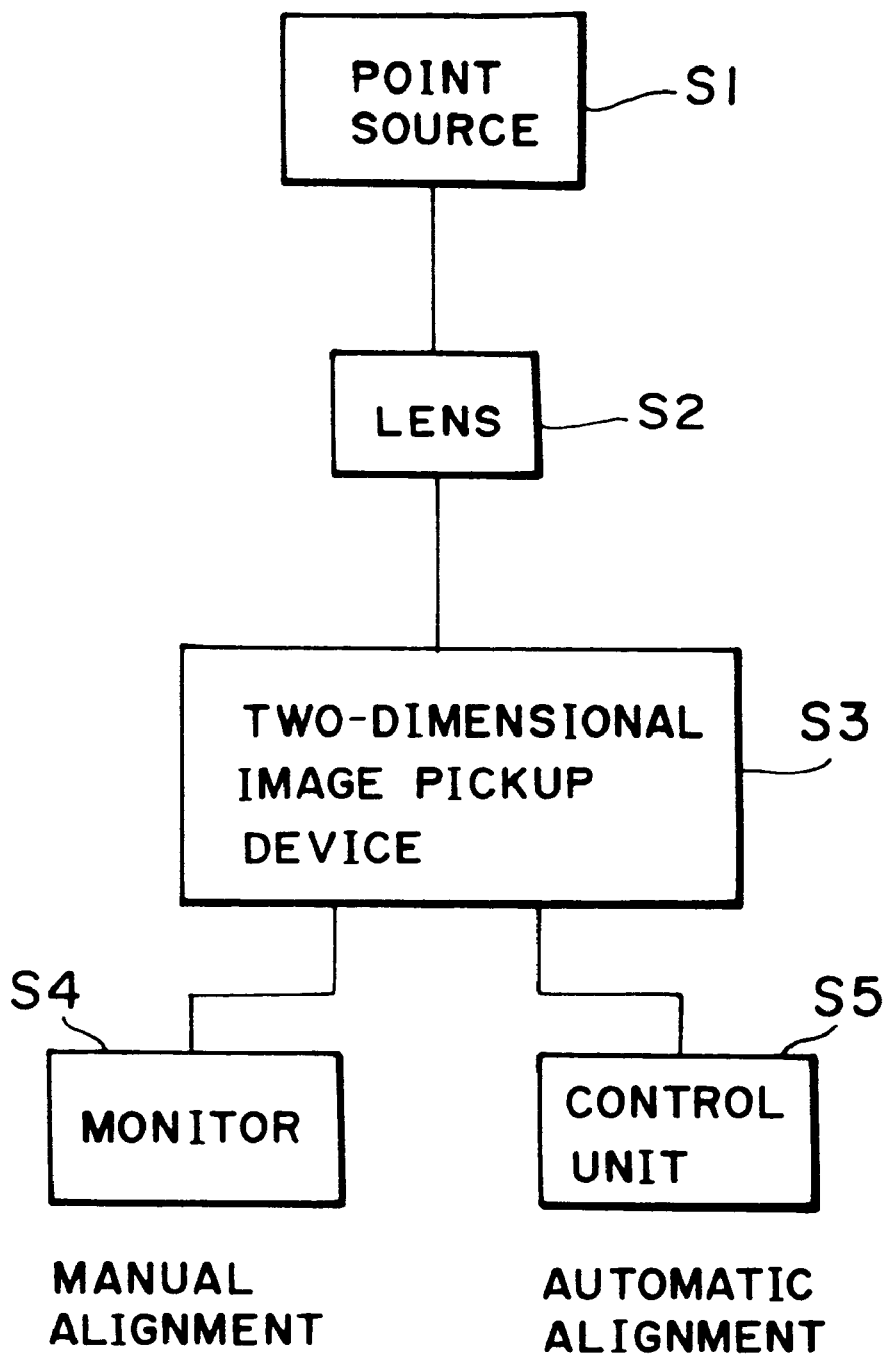

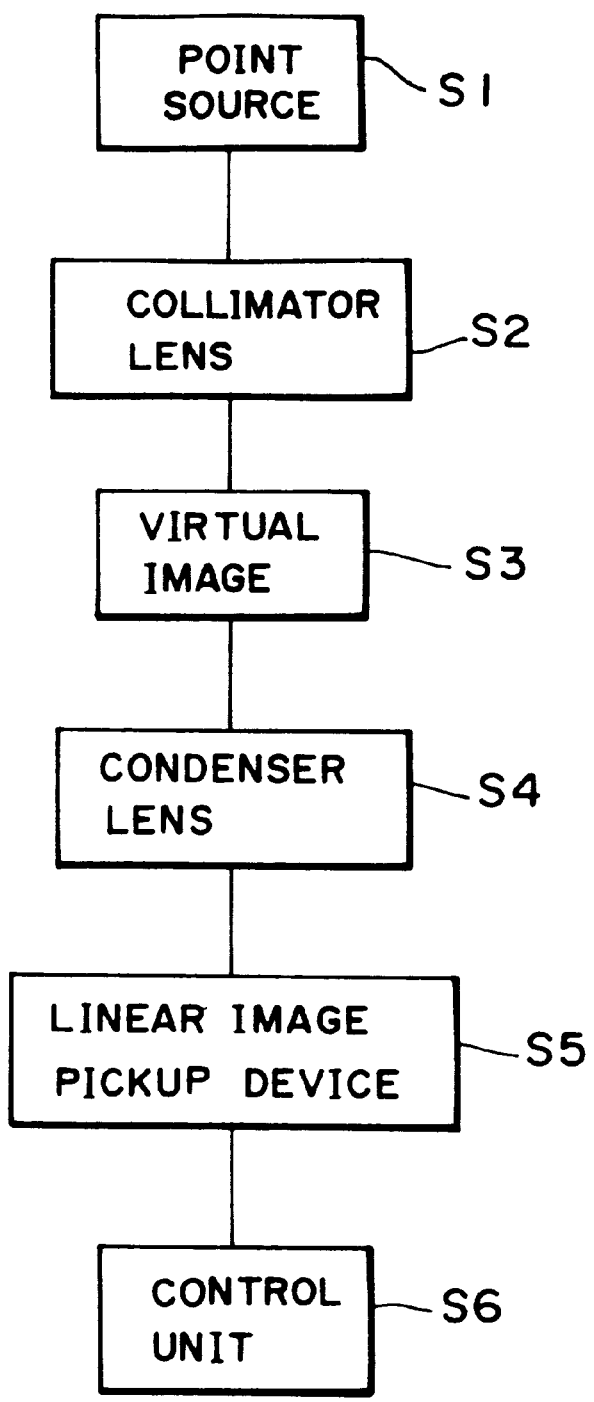

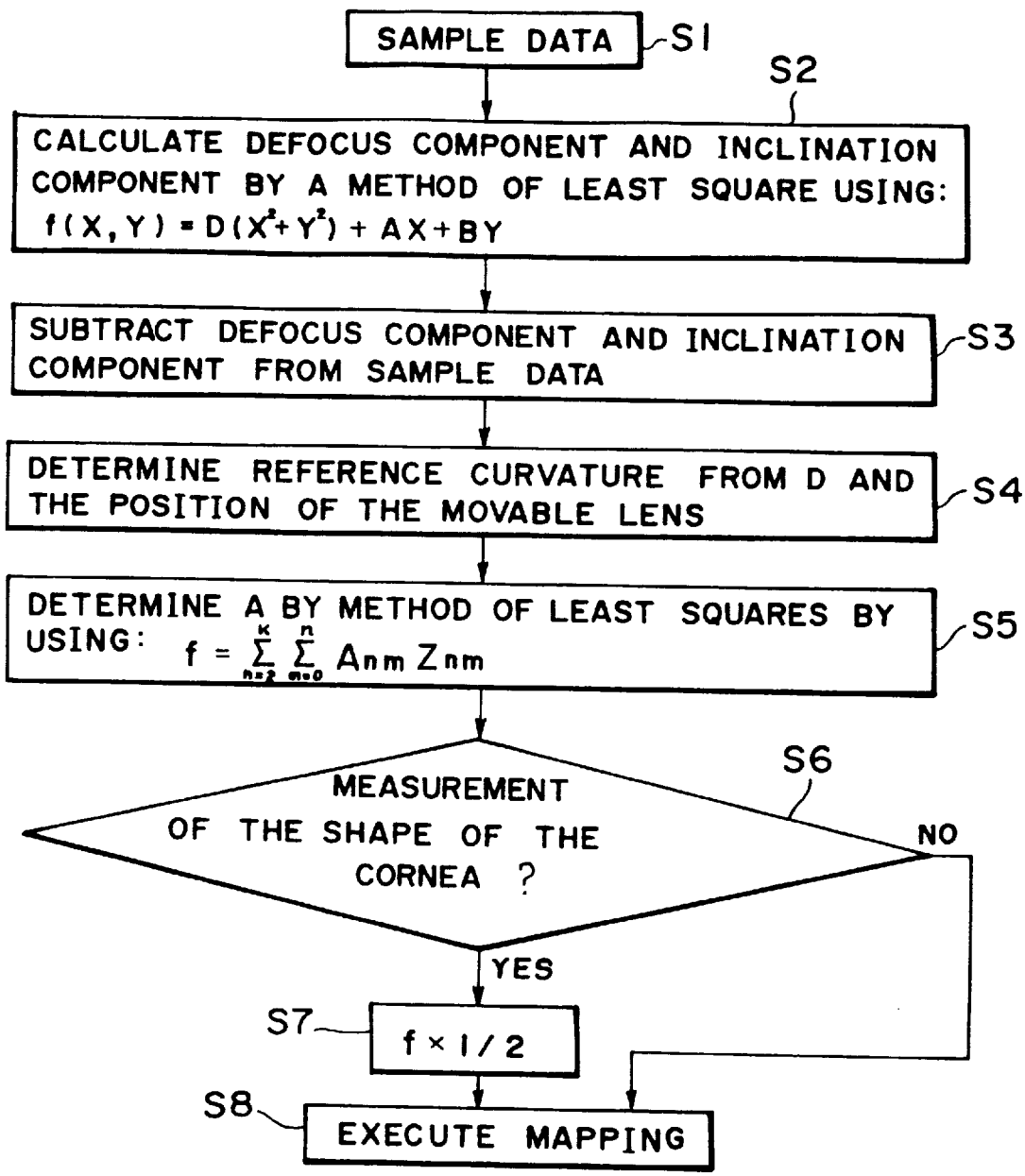

OPTICAL CHARACTERISTIC MEASURING APPARATUS

BACKGROUND OF THE INVENTION

The present invention relates to an apparatus for the precision measurement of the optical characteristics of the eye and the shape of the cornea and, more particularly, to an optical characteristic measuring apparatus capable of measuring optical characteristics of an irregular astigmatism component.

A conventional optical characteristic measuring apparatus for measuring the optical characteristics of the eye known as a refractometer is capable of expressing the optical characteristics of the eye merely as a spherical component, a regular astigmatism component and the angle of the axis of the regular astigmatism component.

Some eyes have an irregular astigmatism component in addition to a regular astigmatism component. Irregular astigmatism cannot be corrected by a pair of spectacles if the quantity of the irregular as astigmatism component is large, contact lens most be used instead of a pair of spectacles lens, the eye must be examined by a medical doctor.

However, the conventional optical characteristic measuring apparatus for measuring the optical characteristics of the eye, such as a refractometer, is used only for reforming a pair of spectacles and its performance is not fully satisfactory. Accordingly, desired eagerly was an appearance of an optical characteristic measuring apparatus capable for accurately measuring the irregular astigmatism component of the eye in addition to the spherical component, the regular astigmatism component and the angle of the axis of the regular astigmatism component.

SUMMARY OF THE INVENTION

An optical characteristic measuring apparatus according to one aspect of the present invention comprises an illuminating optical system for illuminating a minute region on the retina of the eye with light emitted by an illuminating light source; a light receiving optical system for receiving light reflected from the retina of the eye and guiding the reflected light to a light receiving device; a converting device for converting the reflected light into at least seventeen light beams and sending the light beams to the light receiving device; and an arithmetic unit for determining the optical characteristics of the eye and the shape of the cornea of the eye on the basis of the inclination of light rays fallen on the light receiving device.

BRIEF DESCRIPTION OF THE DRAWINGS

FIG. 13 is a flow chart of assistance in explaining XY alignment;

FIG. 14 is flow chart of assistance in explaining Z alignment;

FIG. 16 is a flow chart of assistance in explaining the principle;

DETAILED DESCRIPTION OF THE PREFERRED EMBODIMENTS

First Embodiment

Figure 1A:
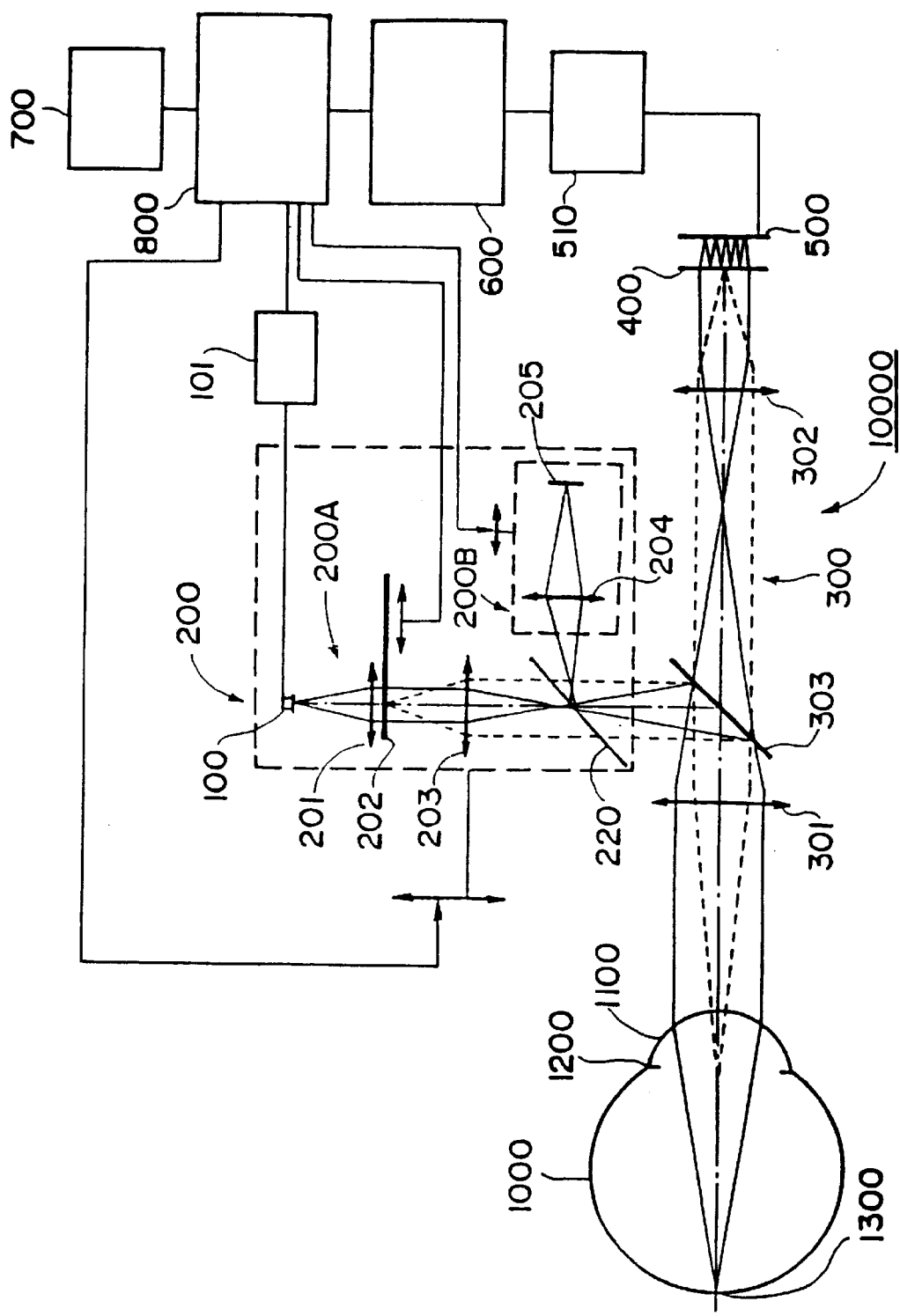
FIG. 1A is a block diagram of an optical characteristic measuring apparatus in a first embodiment according to the present invention.

Referring to FIG. 1A, an optical characteristic measuring apparatus in a first embodiment according to the present invention comprises an illuminating light source 100, an illuminating optical system 200 for illuminating a minute region on the retina of the eye 1000 with light rays emitted by the light source 100, a light receiving device 500 which receives light rays reflected from the retina of the eye 1000, a reflected light guiding optical system 300 for guiding light rays reflected from the retina of the eye to the light receiving device 500, a converting device 400 which converts the reflected light rays into at least seventeen light beams which are received by the light receiving device 500, and an optical characteristic calculating unit 600 which determines the optical characteristics of the eye 1000 on the basis of the inclinations of the light beams determined by the light receiving device 500.

A controller 800 controls operations of the whole electrical configuration of the optical characteristic measuring apparatus including the optical characteristic calculating unit 600. The controller 800 controls and drives the light source 100 through a light source driving unit 101.

It is desirable that the light source 100 is capable of emitting light having a high spatial coherence and a low temporal coherence. The light source 100 of the first embodiment is a SLD (superluminescent diode), which is a point light source having a high luminance.

The light source 100 need not be limited to the SLD (Super Luminescent Diode); a laser which emits light having a high spatial coherence and a high temporal coherence can be employed as the light source 100 it a rotary diffuser or the like is inserted in an optical path to lower the temporal coherence properly.

Although both the spatial coherence and the temporal coherence of the light emitted by a light source such as LED are low, it can be used if a pinhole or the like is disposed at a position corresponding to the light source on the light path, provided that it emits a large quantity of light.

The wavelength of the light emitted by the illuminating light source 100 of the first embodiment may be equal to, for example, that of the B line at the middle of the visible region. Although it is desirable to use the E line, which is a reference wavelength for spectacles, for measurement, the D line may be used for measurement when the optical characteristic measuring apparatus is used in the USA.

The illuminating optical system 200 illuminates a minute region on the retina with the light rays emitted by the light source 100. The illuminating optical system 200 comprises a first condenser lens 201, a variable diaphragm 202, a second condenser lens 203, a fixation point focusing lens 204, and a fixation point 205.

Figure 1B:
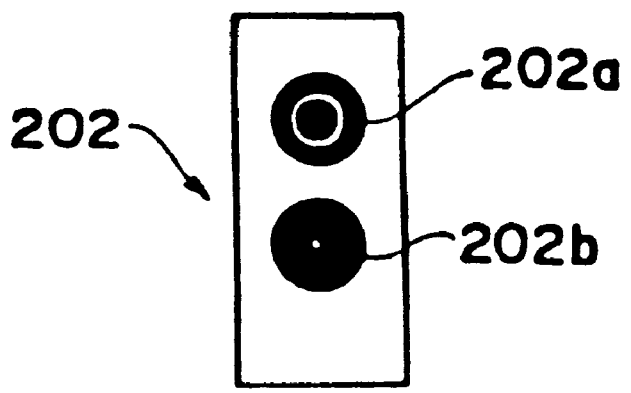
FIG. 1B is a front view of a variable diaphragm included in the optical characteristic measuring apparatus of FIG. 1.

The variable diaphragm 202 is a light screening member. As shown in FIG. 1B, the variable diaphragm 202 is provided with a first diaphragm 202a having an aperture in its peripheral portion, and a second diaphragm 202b having an aperture in its central portion. The first diaphragm 202a and the second diaphragm 202b are arranged side by side. The variable diaphragm 202 is moved in directions perpendicular to its optical axis by a signal provided by the controller 800 to dispose either the first diaphragm 202a or the second diaphragm 202b on the optical path.

Accordingly, the variable diaphragm 202 of the illuminating optical system 200 is able to create a first illuminating state for illumination through a region around the center of the pupil of the eye 1000 and a second illuminating state for illumination through the periphery of the pupil of the eye 1000 at a point substantially conjugate with the pupil of the eye 1000.

The eye 1000 has the cornea 1100, the iris 1200 and the retina 1300.

The variable diaphragm 202 reduces the influence of light reflected by the cornea on measurement.

The reflected light guiding optical system 300 guides the light rays reflected from the retina 1300 of the eye 1000 to the light receiving device 500. The reflected light guiding optical system 300 comprises a first afocal lens 301, a second afocal lens 302, a converting device 400 which converts the reflected light rays into at least seventeen light beams, and a beam splitter 303.

The converting device 400 of the reflected light guiding optical system 300 is conjugate with the variable diaphragm 202 of the illuminating optical system 200. The converting device 400 and the variable diaphragm 202 are conjugate with the iris 1200.

The light reflected from the cornea can be prevented from affecting the measurement of refraction by using a screened portion of the illuminating optical system 200 for the measurement of refraction.

If the first diaphragm 202a of the variable diaphragm 202 is on the optical path, a region corresponding to the central screening portion of the first diaphragm 202a is measured. If the second diaphragm 202b is disposed on the optical path, a region corresponding to a portion around the central aperture is measured.

The illuminating optical system 200 is constructed so that a minute region on the eyeground of the eye 1000 is illuminated by the light emitted by the light source 100 according to the refracting power of the eye 1000 The abnormal refraction of the eye 1000 can be corrected by moving a point light source illuminating system 200A for projecting the light emitted by the light source 100, and an illuminating system including a fixation point projecting system 200 B.

The point light source illuminating system 200A comprises the first condenser lens 201, the variable diaphragm 202 and the second condenser lens 203. The fixation point projecting system 200B comprises the fixation point focusing lens 204 and the fixation point 205. Light rays emitted by the point light source illuminating system 200A and light rays emitted by the fixation point projecting system 200B are combined in coaxial light rays by a beam splitter 220.

The conjugate relationship between the light source 100 and the fixation point 205 is maintained. The illuminating optical system 200 is moved to form images of the point light source and the fixation point 205 on the retina 1300, and then the fixation point projecting system 2003 is moved slightly away from the beam splitter 220 by a signal provided by the controller 800 to blur the image of the fixation point 205.

A first diopter adjusting mechanism adjusts the diopters of the point light source illuminating system 200A and the fixation point projecting system 200B by moving the variable diaphragm 202 and the fixation point 205 respectively along their optical axes so that the level of light received by the light receiving device 500 is kept at a maximum.

One of the objects of the optical characteristic measuring apparatus 10000 in the first embodiment is the measurement of optical characteristics in a state having a specific refractive power at the far point of accommodation, the near point of accommodation or a point between the far point of accommodation and the near point of accommodation.

Accordingly, a minute region on the eyeground is illuminated with light rays according to the variation of the refractive power of the eyes 1000 because, m measurement at the far point of accommodation, for instance, the refractive powers of the eyes 1000 vary in the range of −25 D to 25 D (Diopter) Therefore, the light source 103, the point light source illuminating system 200A and the fixation point projecting system 200B are moved by signals provided by the controller 800.

The reflected light guiding optical system 300 is formed so that the light receiving surface of the light receiving device 500 and the iris 1200 of the eye 1000 are substantially in conjugate relationship with respect to the first afocal lens 301 and the second afocal lens 302.

The converting device 400 will be described hereinafter. The converting device 400 included in the reflected light guiding optical system 300 is a wavefront converting device which converts the reflected light rays into a plurality of light beams. The converting device 400 has a plurality of micro Fresnel lenses arranged in a plane perpendicular to the optical axis.

The micro Fresnel lens will be described in detail.

A micro Fresnel lens is an optical element having annular bands at height pitches for wavelengths and an optimized blaze at a focal point. A micro Fresnel lens which can be applied to the present invention has, for example, eight levels of optical path differences produced by semiconductor fine processing techniques, and is capable of achieving focusing at a focusing efficiency of 98% when only primary light is used.

The converting device 400 of the first embodiment is a wavefront converting device capable of converting the reflected light rays into at least seventeen light beams.

The light receiving device 500 receives a plurality of light beams from the converting device 400. In the first embodiment, the light receiving device 500 is a CCD. The CCD may be a common CCD for TV use or a CCD having 2000×2000 elements for measurement use.

Although a CCD for TV use as the light receiving device 500 has a low resolution, the CCD for TV use is inexpensive and its output can be easily given to a personal computer which is used generally for image processing. NTSC image signals provided by a CCD and its driver can be easily given to a personal computer through an NTSC image input port.

Although a CCD for measurement use having 2000×2000 elements is expensive, analog signals representing measured values can be given to a personal computer if a CCD for measurement use is employed.

Signals provided by a CCD can be converted into corresponding digital signals, and the digital signals may be given to a personal computer.

The reflected light guiding optical system 300 establishes substantially conjugate relationship between the iris 1200 of the eye 1000 and the converting device 400.

The beam splitter 303 is inserted in the reflected light guiding optical system 300 to direct the light transmitted by the illuminating optical system 200 toward the eye 1000, and to transmit the reflected light.

An image signal provided by the light receiving device 500 is given through a light receiving device driver 510 to the optical characteristic calculating unit 600.

The principle of operation of the optical characteristic calculating unit 600 which calculates the optical characteristics of the eye 1000 on the basis of the inclination of light rays determined by the light receiving device 500 will be described hereinafter.

"No relay lens and immovable: Optical characteristics including spherical component are measured"

Emmetropia: Parallel light rays are focused on the eyeground to make a secondary light source on the eyeground emit parallel light rays.

Myopia: Convergent light rays are emitted.

Regular astigmatism: Astigmatism is measured.

Irregular astigmatism: High-order aberration is mixed.

A method of calculation will be described in detail.

Figure 2:
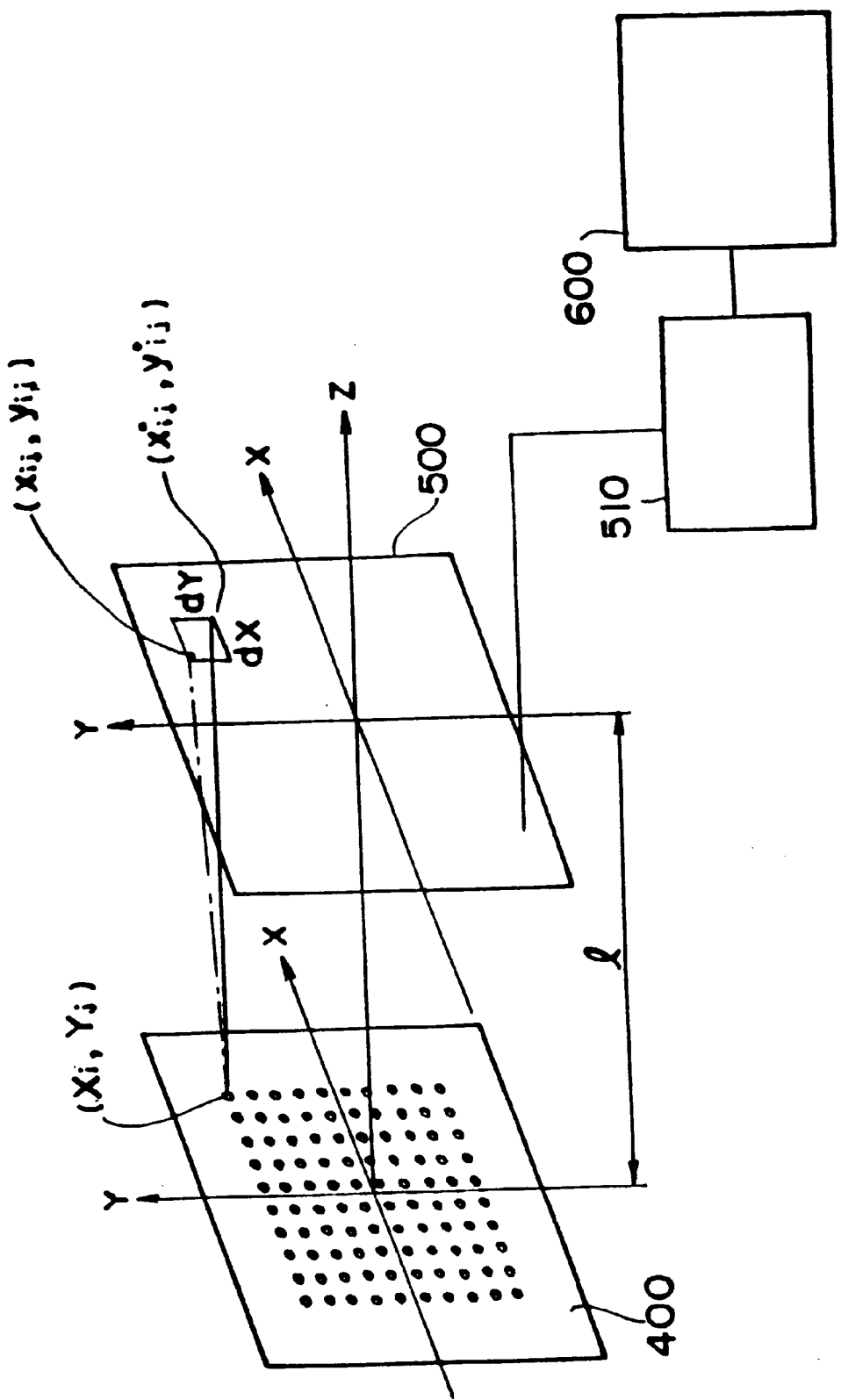
FIG. 2 is diagrammatic view of assistance in explaining the principle of the optical characteristic measuring apparatus of FIG. 1.

As shown in FIG. 2, coordinate axes X and Y are set on the converting device, and coordinate axes x and y are set on the light receiving device 500. Then, a wave surface is expressed by a polar coordinate system or a rectangular coordinate system:

$$w(r, \theta) = W(X, Y) \quad (1)$$

The (i, j)-th measured data is expressed by:

$$w(r_i, \theta_j) = W(X_i, Y_j) \quad (2)$$

The contents of the measured data will be explained later.

The wave surface is expressed by an approximate expression:

$$F(K, G, T, S, C, A, X, Y) = \text{Constant}(K) + \text{Inclination}(G, T, X, Y) + \text{Spherical surface}(S, X, Y) + \text{Regular astigmatism}(C, A, X, Y) \quad (3)$$

The components of this polynomial will be explained.

The constant term is K.

The inclination reflecting alignment error is:

$$Gr\cos(\theta - T) = G\cos(T)X + G\sin(T)Y \quad (4)$$

Spherical surface (Discussion concerning sign)

$$S \pm \sqrt{S^2 - r^2} = S \pm \sqrt{S^2 - (X^2 + Y^2)} \quad (5)$$

Sign is "+" when S is negative and sign is "−" when S is positive.

Regular astigmatism (Discussion concerning sign)

Formula 2 (6)

$$\left(C^2 \pm \sqrt{C^2 - r^2}\right)\cos^2(\theta + A) =$$

$$\left(C \pm \sqrt{C^2 - (X^2 + Y^2)}\right)\left(\frac{\cos^2(A)X^2 + 2\sin(A)\cos(A)XY + \sin^2(A)Y^2}{X^2 + Y^2}\right)$$

Sign is "+" when C is negative and sign is "−" when C is positive.

The square sum of the residuals at each measurement point is:

$$\sum_{i,j} [W(X_i, Y_j) - F(K, G, T, S, C, A, X_i, Y_j)]^2 \quad (7)$$

Values of K, G, T, S, C and A are determined so that a value calculated by Formula 3 is a minimum. The suffixes i and j denotes one of the elements of the converting device 400. Practically, the data represents inclinations and hence the derivative of each wave surface is used for calculation because data measured by the optical characteristic measuring apparatus are the inclination of light rays.

The inclination of light rays can be directly determined by the differentiation of the wave surface by positional coordinates. Values measured by the wavefront sensor are transverse aberrations from a reference.

It is generally known that the following relation holds approximately in FIG. 2.

$$\frac{\partial W(X, Y)}{\partial X} = \frac{dx(X, Y)}{l} \quad (8)$$

$$\frac{\partial W(X, Y)}{\partial Y} = \frac{dy(X, Y)}{l} \quad (9)$$

where l is the distance between the converting device 400 and the light receiving device 500. "Wave surface, and transverse aberration measured by the wavefront sensor"

Values dx(X, Y) and dy(X, Y) are calculated for each element of the converting device 400, having a center point at X, Y, in which dx and dy are distances along the x-axis and the y-axis between a predetermined origin on the light receiving device 500, and a point on the light receiving device 500 where the light beam falls on the light receiving device 500. As shown in FIG. 2, an origin corresponding to one element of the converting device 400 is a point on the light receiving device 500 where the converted light rays can be measured when both the spherical component and the astigmatism component representing the refractive characteristic of the eye are 0 diopter, and there is no residual of irregular astigmatism, which will be described later.

Suppose that the position of each point is $(x^0, y^0)$ when S, C and A are zero and there is no residual aberration. Then, $$dx(X_i, Y_j) = x_{ij} - x^0_{ij} \quad (10)$$

$$dy(X_i, Y_j) = y_{ij} - y^0_{ij} \quad (11)$$

Therefore, at the time of using the differentiation, the square sum of the the residuals is:

$$\sum_{i,j} \left[ \left\{ \frac{dx(X_i, Y_j)}{l} - \left(\frac{\partial F}{\partial X}\right)_{(X_i, Y_j)} \right\}^2 + \left\{ \frac{dy(X_i, Y_j)}{l} - \left(\frac{\partial F}{\partial Y}\right)_{(X_i, Y_j)} \right\}^2 \right] \quad (12)$$

The parameters G, T, S and C of F which makes the residual a minimum may be determined by an appropriate nonlinear optimizing method, such as a method of attenuation least squares.

The values of K, G and T are considered to reflect measuring errors. In an auto-refractometer, S, C and A are measured values.

Although signs of some terms in the expressions expressing a spherical surface and regular astigmatism are indefinite, combinations may be calculated individually and a case where the residual is the smallest may be employed.

A Irregular Astigmatism Component

The differentiation residuals are irregular astigmatism component.

The conventional auto-refractometer is unable to measure the residual component, and a new piece of software is necessary.

When analyzing the residual, i.e., the irregular astigmatism component, (1) The residual is calculated and represented in the form of the square sum.

(2) The residual is divided into components by a method similar to a method known in the theory of aberration.

(3) All the deviations from the wave surface expressed by S, C and A as a reference surface are provided.

In some cases, a reference wave surface expressed by S or a reference wave surface represented by a plane is necessary to find out the distortion of the wave surface if the irregular astigmatism is large.

"Square Sum of Residuals"

The square sum of residuals is measured by using K, G, T, S, C and A determined by the foregoing method. If the square sum of residuals has N rows and M columns, a measurement value of the square sum of residuals is obtained by dividing the square sum of residuals by a value obtained by doubling the square of $n = N \times M$.

$$\frac{\sum_{i,j} \left[ \left\{ \frac{dx(X_i, Y_j)}{l} - \left(\frac{\partial F}{\partial X}\right)_{(X_i, Y_j)} \right\}^2 + \left\{ \frac{dy(X_i, Y_j)}{l} - \left(\frac{\partial F}{\partial Y}\right)_{(X_i, Y_j)} \right\}^2 \right]}{2n} \quad (16)$$

B Analysis of Components

Comatic aberration: $r^{(2n+1)}\cos(\theta + T_n)(n=1, 2, \ldots)$

Spherical aberration: $r(n=2, 3, \ldots)$

High-order astigmatism: $r^{2n}\cos^2(\theta + A_n)(n=1, 2, \ldots)$

There is an important aberration of an order higher than that of t astigmatism component in the direction of rotation $$f(r)\cos^n(\theta + T_n)(n=3, \ldots)$$

The parameters of these terms are deter by subtracting values contributed to the components of the inclination, the spherical surface and the regular astigmatism by G, T, S, C and A obtained previouly from the inclination of light rays. The comatic aberration, the spherical aberration, the high-order astigmatism and other contribution can be calculated.

C Output of Deviation from Reference Wave Surface

The distance dL between corresponding positions on the reference wave surface F' and the actual wave surface F is indicated.

In the following description, Fb and Pr are obtained by removing terms of constants and inclination from F.

These are expressed by functions approxiating wave surfaces.

(Reference wave surface) = $W_b(X_i, Y_j) = F_b(S, C, A, X_i, Y_j)$ (Reconstructed wave surface) = $W_r(X_i, Y_j) = F_r(S, C, A,$ parameters of irregular astigmatism component, $X_i, Y_j)$ $$\Delta z_{ij} = W_r(X_i, Y_j) - W_b(X_i, Y_j) \quad (17)$$

All the indications can be expressed in a unit of wavelength or a unit of micrometer.

D Indication of Deviation of Power from Reference Wave Surface (1) Power is calculated on the basis of the respective calculated residuals of the components.

(2) The inclination dependent only the residual component at that point is determined on the basis of only the residual component.

(3) The inclination at that point calculated on the basis of the reference wave surface Wb is subtracted from the measured value, and the power of a point is calculated on the basis of points, typically, eight or fifteen points, around the point.

Figure 3:
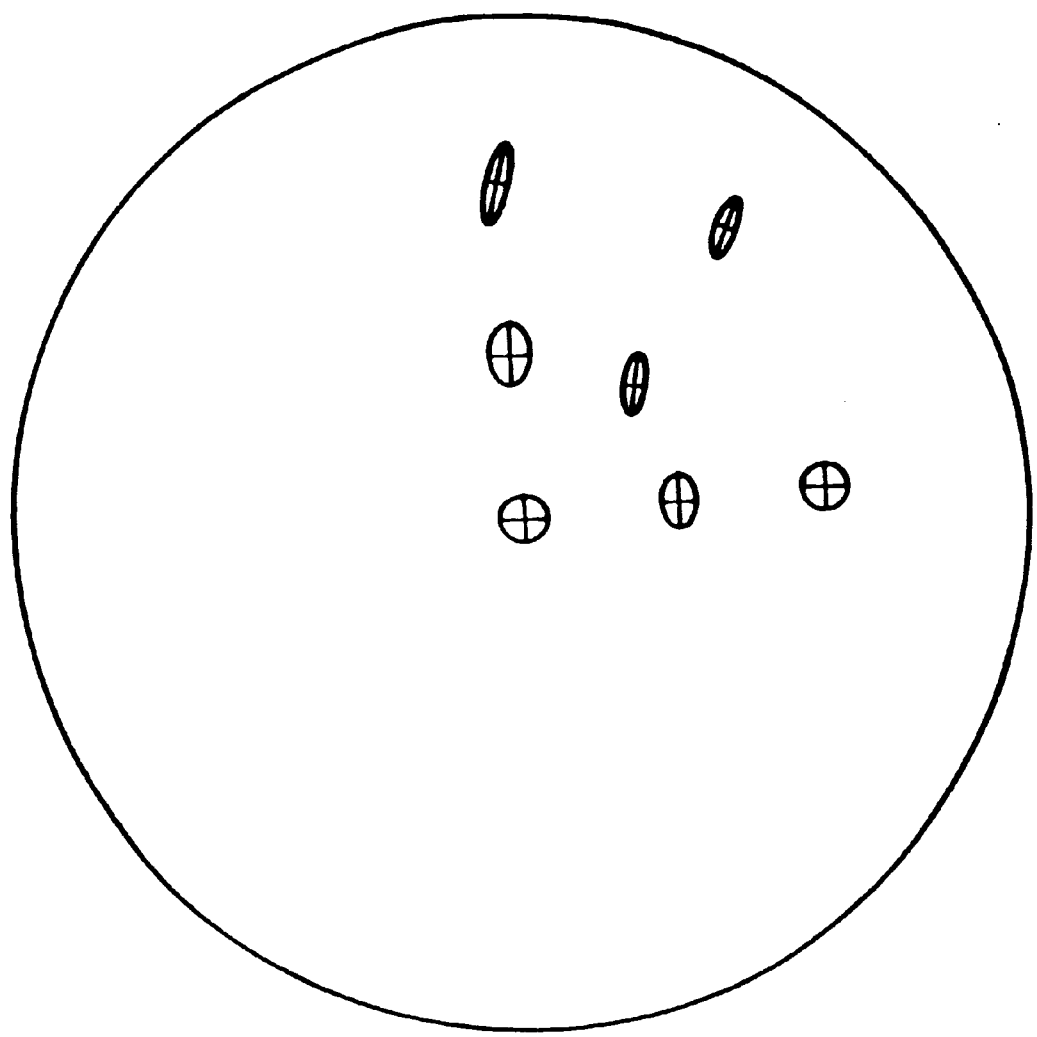
FIG. 3 is a diagrammatic view of assistance in explaining a method of directly indicating power based on quantity and orientation relating to maximum curvature and minimum curvature.

As shown in FIG. 3, the power indicates directly a quantity and an orientation relating to the maximum and the minimum curvature at a point on a geometrical curved surface. When light rays converge in a radius R of curvature, power is expressed by 1/R.

Figure 4:
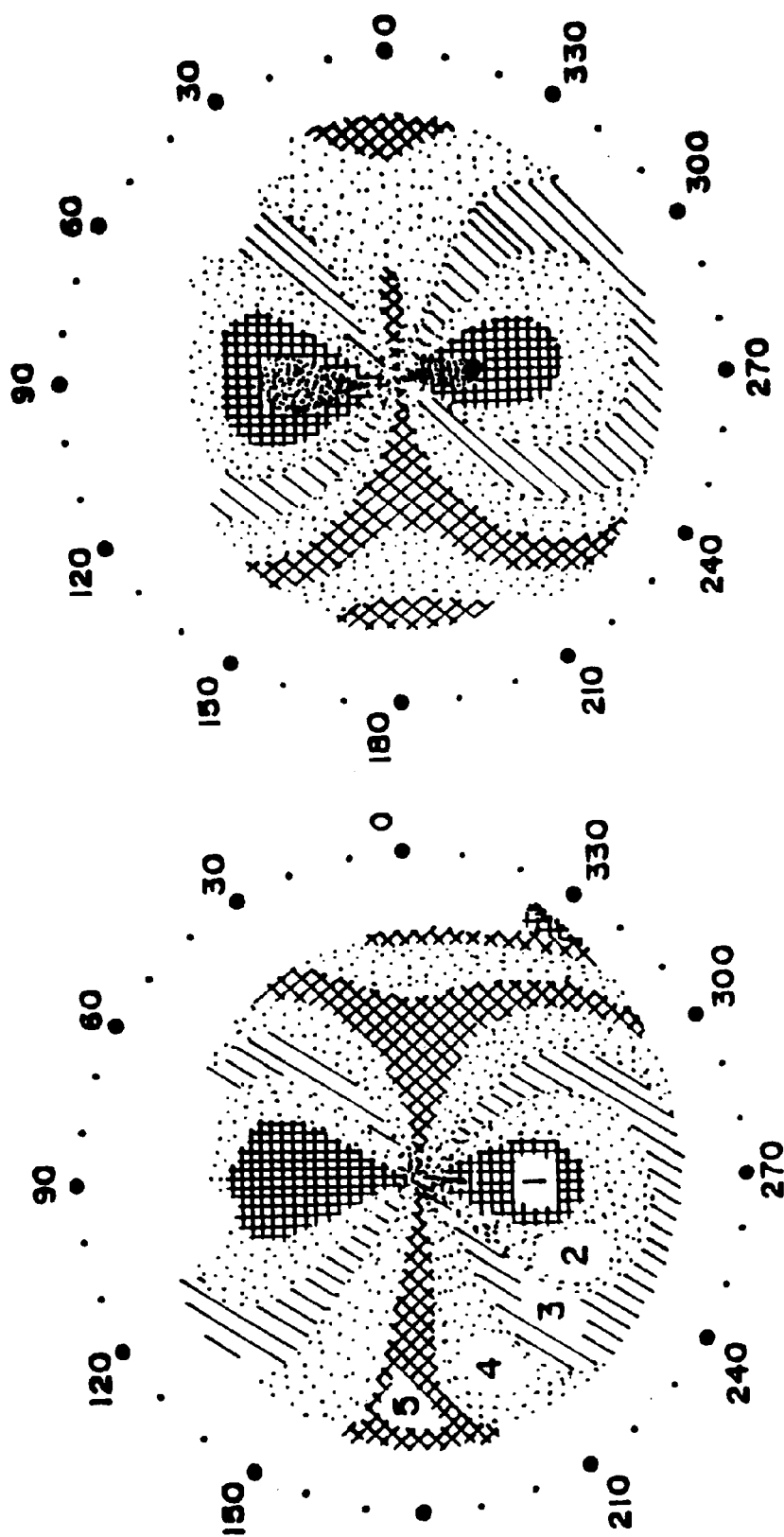
FIG. 4 is a pictorial view of assistance in explaining a method of indicating meridional power.
Figure 5:
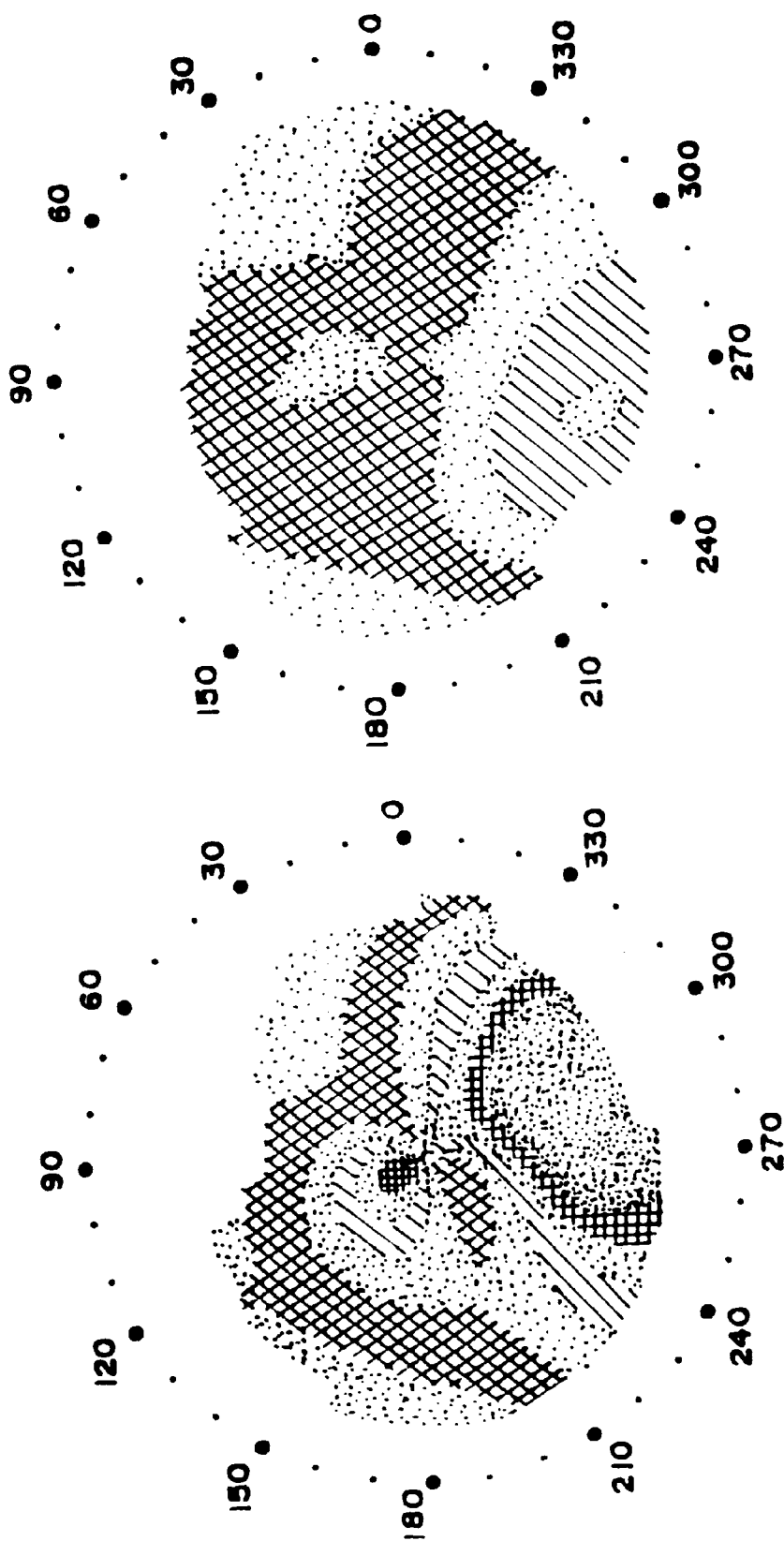
FIG. 5 is a pictorial view of assistance in explaining a method of indicating meridional power.
Figure 7A:
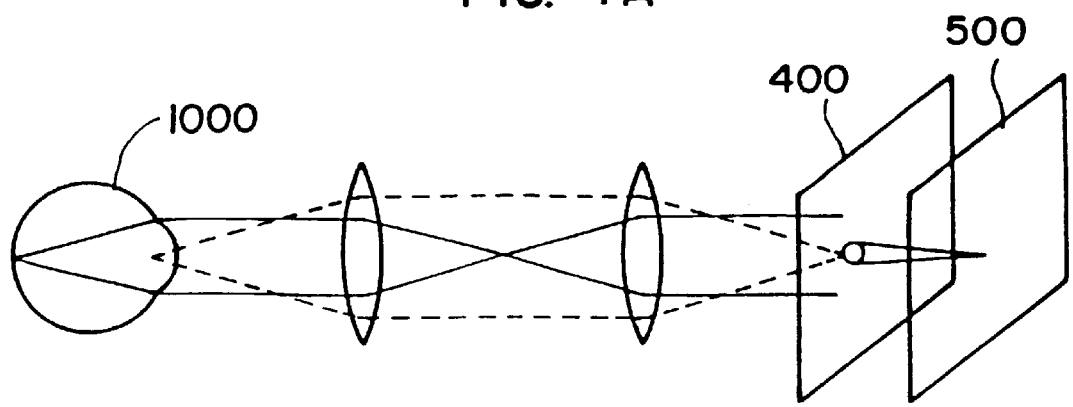
FIG. 7(a) is a diagrammatic view of assistance in explaining a method of discriminating between an image formed by light reflected from the retina and an image formed by light reflected from the cornea.
Figure 7B:
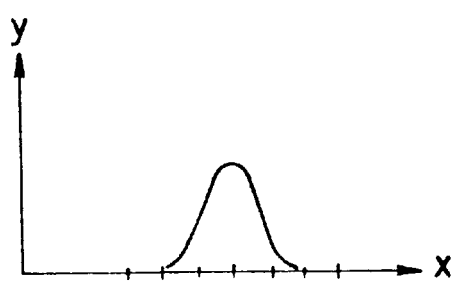
FIGS. 7(b) to 7(d) are graphs of assistance in explaining a method of discriminating between an image formed by light reflected from the retina and an image formed by light reflected from the cornea.
Figure 7C:
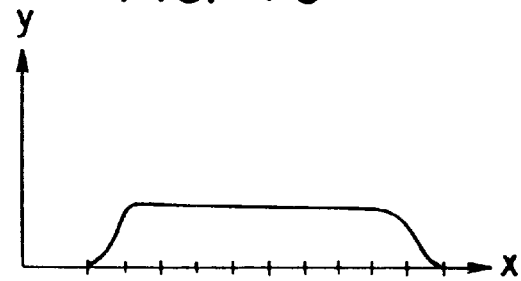
Figure 7D:
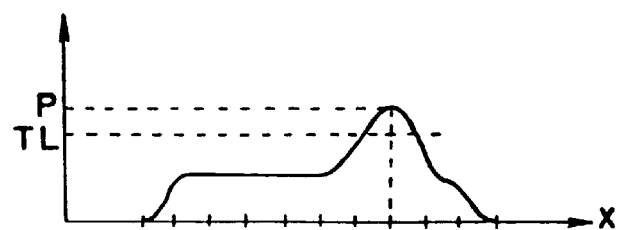

Meridional power is indicated by a method illustrated in FIGS. 4 and 5.

Generally, regular astigmatism has a high power in the direction of the vertical meridian and a low power in the direction of the horizontal meridian. Power is expressed in diopters.

The operation of the converting device 400 for converting the reflected light rays into at least seventeen light beams will be described in detail.

When measuring the S, C and A component, the origin and one point on a radius, the direction of rotation can be calculated on the basis of data on four points. Since at least information of an order higher than that by one order is necessary, seventeen measuring points, i.e., a summation of 2×8=16 points and the origin, are necessary.

Accordingly, the optical characteristic calculating unit 600 determines the inclination of light rays from a position on which the primary light rays are converged by the plurality of micro Fresnel lenses, and determines the optical characteristics of the eye 1000 on the basis of the inclination of light rays.

A blurred image is formed at one point represented by data on received light rays if the converting device 400 does not use the micro Fresnel lenses, and hence the center of gravity of each point is determined.

Figure 6:
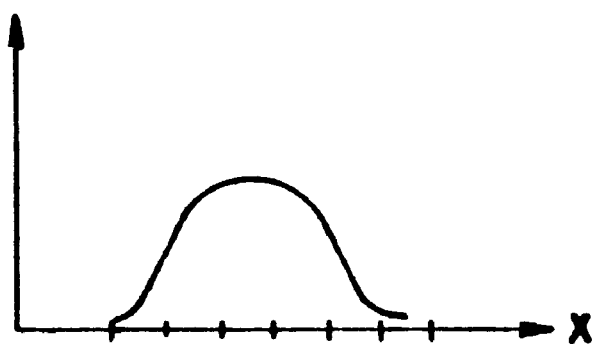
FIG. 6 is a graph of assistance in explaining a method of improving the accuracy of position measurement.

Even if micro Fresnel lenses are used, the accuracy of position measurement can be increased by observing an image intentionally blurred by the light receiving elements as shown in FIG. 6. The position of the center of gravity can be determined by making the projected light rays fall on a plurality of pixels on the light receiving surface and making reference to the intensities of light rays fallen on the pixels.

The accuracy of position measurement not higher than 1/10 of the element can be secured by thus calculating the position of the center of gravity.

As shown in FIG. 7, since an image formed by light rays reflected from the retina and an image formed by light rays reflected from the cornea are different in the degree of blur and hence those images can be discriminated from each other.

In an arrangement shown in FIG. 7(*a*), FIG. 7(*b*) is a graph showing the distribution of intensity of light rays reflected from the retina on the light receiving device 500, FIG. 7(*c*) is a graph showing the distribution of intensity of light rays reflected from the cornea on the light receiving device 500, and FIG. 7(*d*) is a graph produced by combining distribution curves shown in FIGS. 7(*b*) and 7(*c*).

When discriminating the images from each other, a peak is detected, a slice level slightly lower than that of the peak is set, and the position of the light rays reflected from the retina is determined without being affected by the light rays reflected from the cornea. The position of the light rays reflected from the retina can be determined by using an appropriate filter.

The optical characteristic measuring apparatus may be provided with a display unit 700 for displaying the results of arithmetic operations carried out by the optical characteristic calculating unit 600.

The display unit 700 are capable of displaying the optical characteristics of the eye 1000 in the spherical component, the regular astigmatism component, the angle of the axis of the regular astigmatism component, and the irregular astigmatism component, which are determined by calculation by the optical characteristic calculating unit 600.

Examples will be given below.

(1) Display of Irregular Astigmatism Component

The irregular astigmatism component indicates a comatic component, a spherical aberration component and a high-order astigmatism component.

(2) Display of Irregular Astigmatism Component as Deviation

The irregular astigmatism component indicates two-dimensionally deviation from the wave surface consisting of only a spherical component and a rear astigmatism component.

(3) Two-Dimensional Display of Curvature of Wave Surface in Diopters

Two-dimensional graphic display is possible. A point having astigmatism has two curvatures. According to the teachings of differential geometry, both are perpendicular to each other.

The display unit 700 is capable of graphically displaying the optical characteristics of the eye 1000. The display unit 700 is capable of displaying a picture of the eye 1000 viewed from the front on an x-y coordinate system and of mapping powers in, for example, diopters on an x-y coordinate system.

The display unit 700 is capable of displaying the deviations of the optical characteristics of the eye 1000 from those of the normal eye.

The display unit 700 is also capable of mapping the deviations from a reference wave surface reproduced from the calculated values of S, C and A on the order of wavelength on the x-y coordinate system.

The display unit 700 is capable of graphically displaying deviations of the optical characteristics of the eye 1000 from those of the normal eye, and those data can be represented in contour.

The display represented in contour can be mapped by, for example, pseudocolors.

Figure 19A:
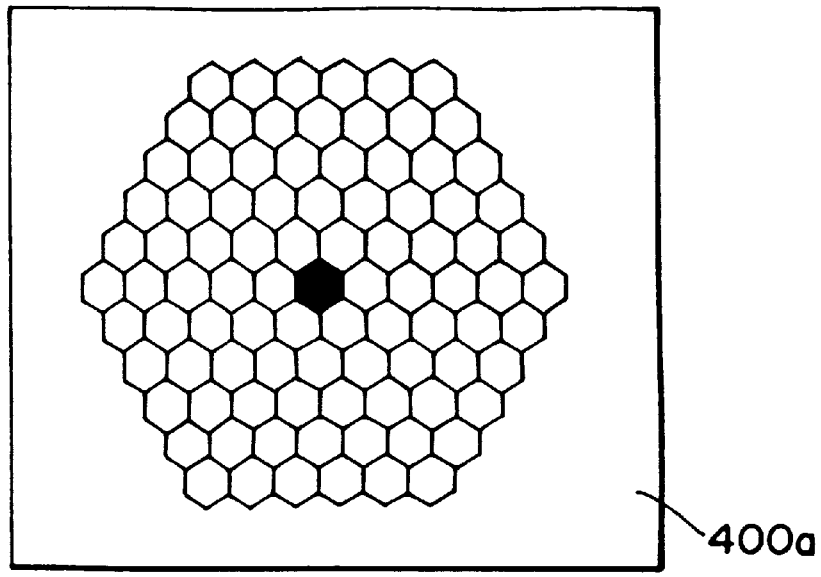
FIG. 19 is a pictorial view of assistance in explaining the function of an optical characteristic measuring apparatus in a modification of the optical characteristic measuring apparatus in the first embodiment.
Figure 19B:
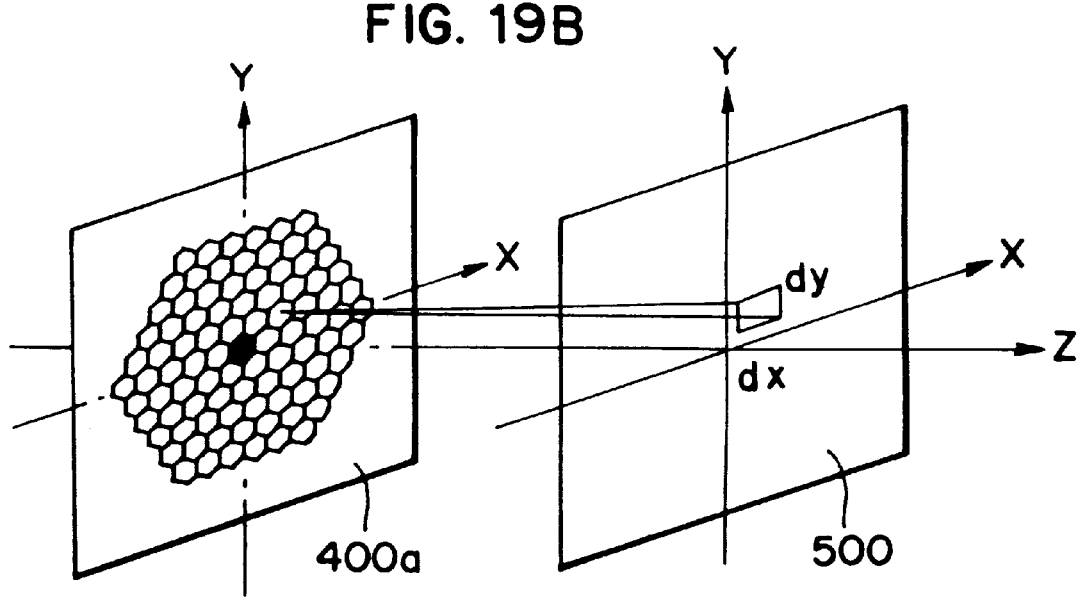

Although the converting device 400 employed in the first embodiment is a Hartmann plate employing micro Fresnel lenses, the converting device 400 may be a Hartmann plate employing honeycomb-shaped micro Fresnel lenses as shown in FIGS. 19(*a*) and 19(*b*). A honeycomb-shaped converting device 400*a* is constructed so that a portion on the optical axis of the reflected light guiding optical system 300 is indicated by a signal provided by the light receiving device 500. A portion of the Hartmann plate on the optical axis of the reflected light guiding optical system 300 is chromium-plated to form a screening portion.

The respective origins of the X-Y coordinate system on the converting device 400*a* and the x-y coordinate system on the light receiving device 500 can be easily determined on the basis of positions corresponding to the screening portion of the converting device 400 in the signal provided by the light receiving device 500.

Second Embodiment

The optical characteristic measuring apparatus 10000 in the first embodiment includes the Hartmann plate provided with micro Fresnel lenses as the converting device 400. An optical characteristic measuring apparatus 10000 in a second embodiment according to the present invention employs a liquid crystal device 410 as a converting device 400 instead of the Hartmann plate provided with micro Fresnel lenses.

Apertures for passing light rays can be formed in an optional portions of the liquid crystal device 410. For example, the resolution of a liquid crystal device of the SVGA (super video graphics array) system is 800 dots by 600 dots.

Figure 8:
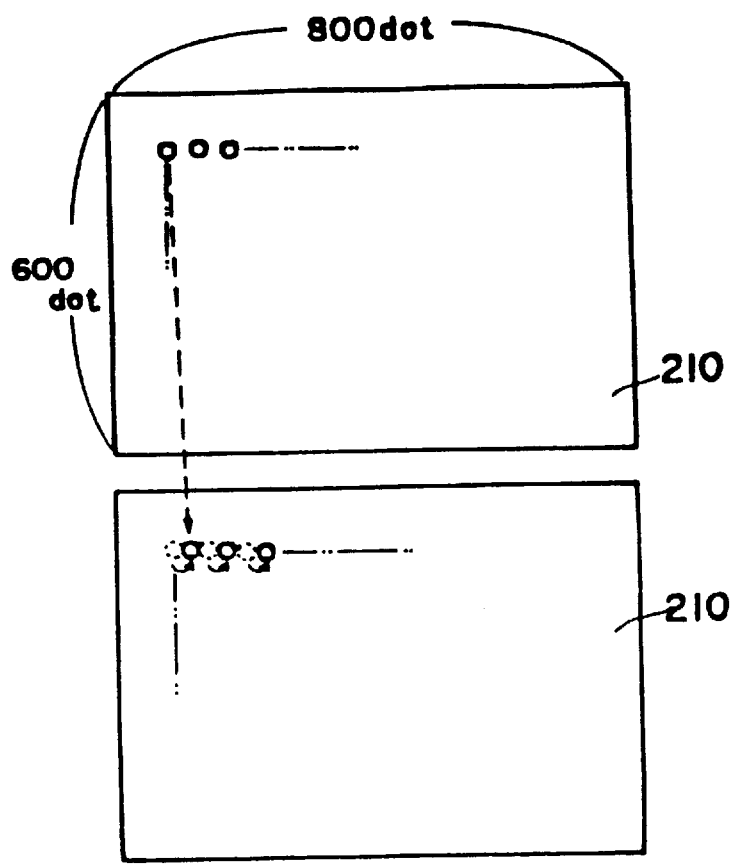
FIG. 8 is a diagrammatic view of assistance in explaining a liquid crystal device.

As shown in FIG. 8, the liquid crystal device 410 is driven by the following method.

The actions of the liquid crystal device 410 are similar to those of the converting device 410 employed in the first embodiment.

First, measurement 1 is carried out in this state.

Then, all apertures are shifted laterally by half the spatial period of the apertures and measurement 2 is carried out.

Subsequently, all the apertures are shifted longitudinally by half the spatial period. and measurement 3 is carried out.

All the apertures are shifted laterally by half the spatial period in a direction reverse to that in which the apertures were shifted laterally in the first lateral shifting cycle and measurement 4 is carried out.

Consequently, the number of measuring points is four times as large as the number of measuring points at the measurement 1.

Generally, the following is possible.

Suppose that the apertures are square apertures of a size corresponding to 10 dots by 10 dots for simplicity. Then, information about different position s o n the iris can be obtained by shifting the apertures by a distance corresponding to one dot at a time.

Thus information about 791 dots by 691 dots can be obtained.

Third Embodiment

Figure 9:
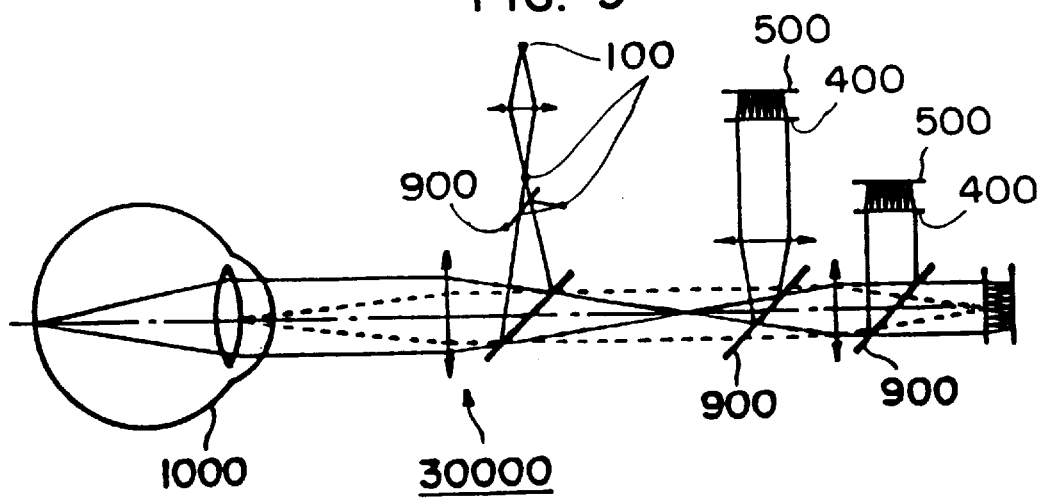
FIG. 9 is a diagrammatic view of an optical characteristic measuring apparatus in a third embodiment according to the present invention.

As shown in FIG. 9, an optical characteristic measuring apparatus 30000 in a third embodiment according to the present invention uses R, G and B light rays for the precision measurement of the optical system of the eye 1000. Measurement using the center wavelengths of cones. for the three primaries.

(1) Two dichroic mirrors 900 are disposed between the last lens of a reflected light guiding optic system and a converting device 400, reflected light rays are divided by wavelength into R, G and B light rays, and the R, G and. B. light rays are received by three light receive devices 500, respectively.

(2) A color CCD may be used as the light receiving device 500.

Light rays of the d line may be used for measurement when the optical characteristic measuring apparatus is used in the USA.

Fourth Embodiment

Figure 10:
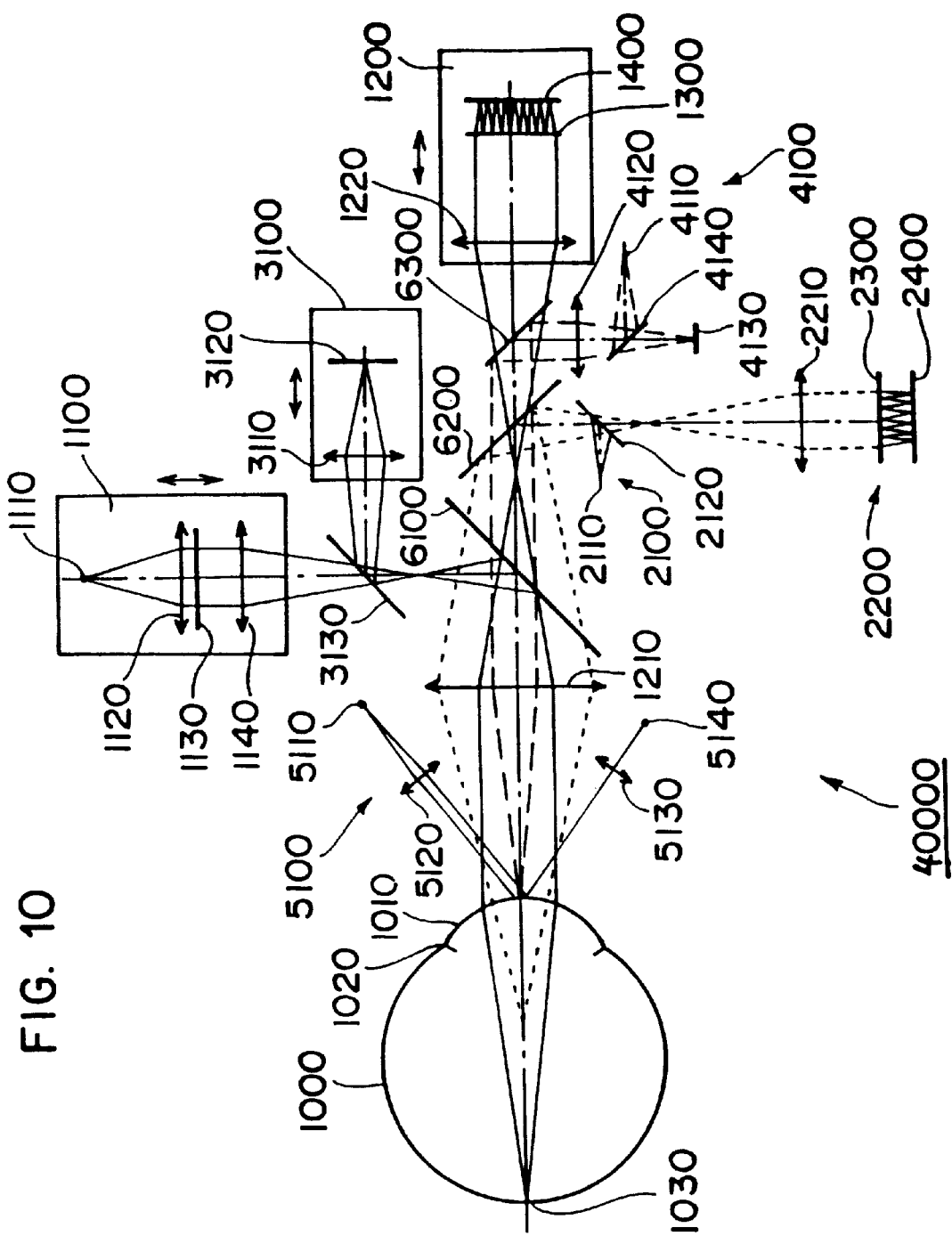
FIG. 10 is a diagrammatic view of an optical characteristic measuring apparatus in a fourth embodiment according to the present invention.
Figure 11:
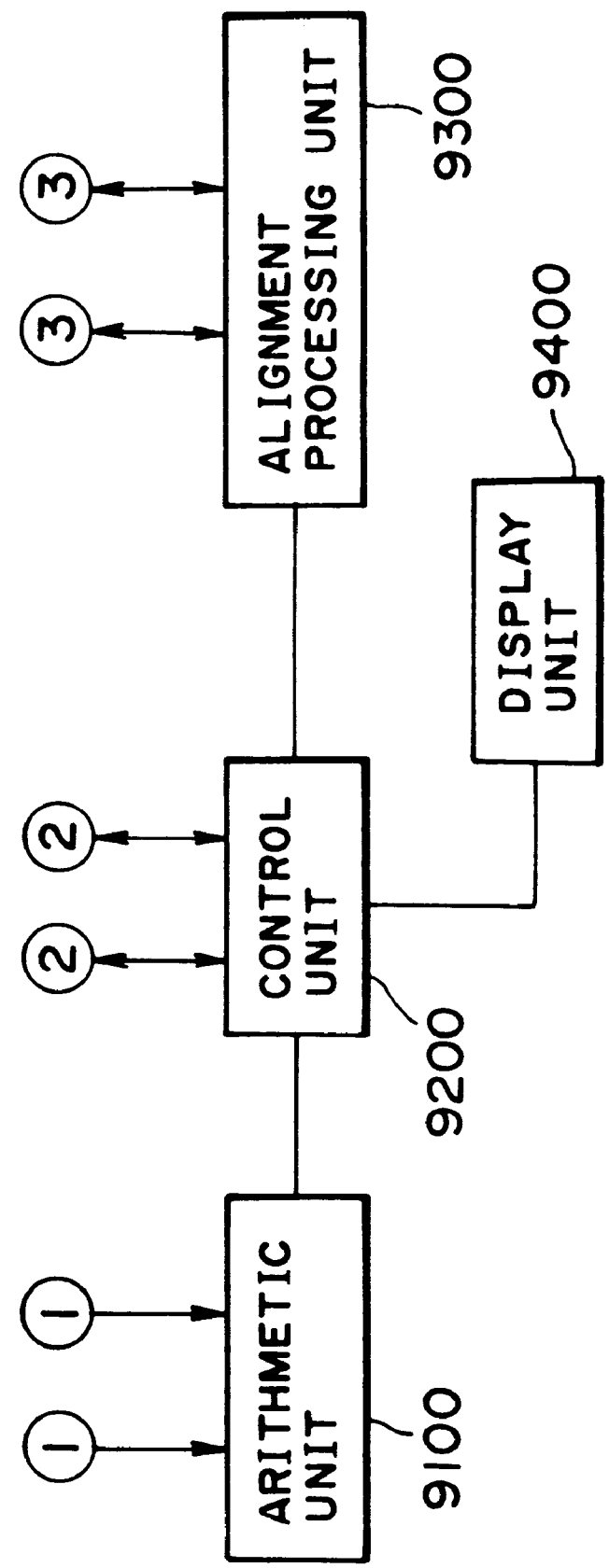
FIG. 11 is a block diagram showing the electrical configuration of the optical characteristic measuring apparatus in the fourth embodiment.

Referring to FIGS. 10 and 11, an optical characteristic measuring, apparatus 40000 in a fourth embodiment according to the present invention comprises a first light source 1110 which emits light rays of a first wavelength, a first illuminating optical system 1100 for illuminating a minute region on the retina 1030 of the eye 1000 with light rays emitted by the first light source 1110, a first reflected light guiding optical system 1200 for guiding light rays reflected by the retina, a first converting device 1300 for converting the reflected light rays into at least seventeen light beams, a first light receiving device 1400 which receives a plurality of light beams from the first converting device 1300, a second light source 2110 which emits light rays of a second wavelength different from the first wavelength, a second illuminating optical system 2100 which focuses light rays emitted by the second light source 2110 for illumination on a portion of the eye 1000 around the center of curvature of the cornea of the eye 1000, a second reflected light guiding optical system 2200 for guiding light rays reflected from the cornea of the eye 1000, a second converting device 2300 which converts the light rays reflected from the cornea into at least seventeen light beams, a second light receiving device 2400 which receives a plurality of light beams from the second converting device 2300, and an arithmetic unit 9100 which determines the optical characteristics of the eye 1000 on the basis of the inclination of light rays received by the first light receiving device 1400, and determines the shape of the cornea of the eye 1000 on the basis of the inclination of light rays received by the second light receiving device 2400.

The first illuminating optical system 1100 illuminates a minute region on the retina of the eye 1000 with light rays emitted by the first light source 1110. The first illuminating optical system 1100 comprises a first condenser lens 1120, a light screening member 1130 and a second condenser lens 1140.

The first illuminating optical system 1100 can be moved along its optical axis according to the refractive power of the eye 1000 to focus light rays on the eyeground of the eye. The first illuminating optical system 1100 of the optical characteristic measuring apparatus 40000 can be moved along its optical axis in a distance range corresponding to a range of about −20 D to about +20 D.

It is desirable that the first light source 1110 is capable of emitting light having a high spatial coherence and a low temporal coherence. The first light source 1110 of the fourth embodiment is a SLD, which is a point light source having a high luminance.

The first light source 1110 need not be limited to the SLD; a laser which emits light having a high spatial coherence and a high temporal coherence can be employed as the first light source 1110 if a rotary diffuser or the like is inserted in an optical path to lower the spatial coherence and the temporal coherence properly.

Although both the spatial coherence and the temporal coherence of the light emitted by a light source such as LED are low, it can be used if a pinhole or the like is disposed at a position corresponding to the light source on the light path, provided that the SLD emits a large quantity of light.

The first wavelength of the light emitted by the first light source 1110 may be a wavelength in the infrared region, such as 840 nm.

The light screening member 1130 is used for creating an illuminating state 1A in which the eye is illuminated through a portion thereof around the pupil, and an illuminating state 1B in which the eye is illuminated through a portion thereof around the center of the pupil.

The light screening member 1130 may be a variable diaphragm provided with a first diaphragm having an aperture in its central portion for creating the illuminating state 1B, and a second diaphragm having an aperture in its peripheral portion for creating the illuminating state 1A.

A screened portion of the first illuminating optical system 1100 is used for the measurement of refraction to achieve measurement without being affected by light rays reflected from the cornea.

When the first diaphragm of the variable diaphragm is disposed on the optical path, a range corresponding to a central screened portion is measured. When the second diaphragm of the variable diaphragm is disposed on the optical path, a range corresponding to a region around the central aperture is measured.

The light screening member 1130 may be a liquid crystal device capable of forming an aperture in its central portion to set the illuminating state 1A and of forming an aperture in its peripheral portion to set the illuminating state 1B.

Accordingly, the light screening device 1130 of the first illuminating optical system 1100 is at a point substantially conjugate with the pupil of the eye 1000, and is capable of creating the first illuminating state 1A for illumination through a region around the center of the pupil of the eye 1000 and the second illuminating state 1B for illumination through the periphery of the pupil of the eye 1000.

The eye 1000 has the cornea 1010, the iris 1020 and the retina 1300.

The first reflected light guiding optical system 1200 guides light rays reflected from the retina 1030 of the eye 1000 to the light receiving device. The first reflected light guiding optical system 1200 comprises a first afocal lens 1210, a second afocal lens 1220, and a first converting device 1300 for converting the reflected light rays into at least seventeen light beams.

Movement of the first illuminating optical system 1100 and the first reflected light guiding optical system 1200 is coordinated so that the positional relation between the first illuminating optical system 1100 and the first reflected light guiding optical system 1200 which makes a signal provided by the first light receiving device 1400 when the reflected light rays reflected from a point on which the light rays emitted by the first light source 1110 are focused fall thereon reach a peak is maintained. The first illuminating optical system 1100 and the first reflected light guiding optical system 1200 are moved in directions to increase the peak of the output signal of the first light receiving device 1400 and are stopped at positions where the intensity of the light rays falling on the first light receiving device 1400 is a maximum. Consequently, light rays emitted by the first light source 1110 are focused on the retina 1030.

The first converting device 1300 of the first reflected light guiding optical system 1200 is conjugate with the light screening member 1130 of the first illuminating optical system 1100. The first converting device 1300 and the light screening member 1130 are conjugate with the iris 1200.

The first reflected light guiding optical system 1200 is moved along the optical axis according to the refractive power of the eye 1000. The first light receiving device 1400 or the first converting device 1300 is substantially conjugate with the cornea 1010.

As shown in FIG. 11, the arithmetic unit 9100 is connected to a control unit 9200 and carries out operations for calculating optical characteristics according to instructions given thereto by the control unit 9200.

The control unit 9200 controls the optical characteristic measuring apparatus including the arithmetic unit 9100. An alignment processing unit 9300 controls an alignment process.

A display unit 9400 displays data provided by the arithmetic unit 9100. The display unit 9400 is capable of displaying the calculated optical characteristics of the eye 1000 calculated by the arithmetic unit 9100 and the shape of the cornea 1010.

The arithmetic unit 9100 estimates the optical characteristics of the eye 100 from the shape of the cornea 1010, compares the estimated optical characteristics with measured optical characteristics determined on the basis of the output of the first light receiving device 1400 to find abnormal optical characteristics attributable to the shape of the cornea 1010. The optical characteristics can be calculated by a ray tracing method or a simpler approximation method. The position of a secondary point source on the retina 1030 may use a model value from the S value of refraction measurement at that time.

Figure 12:
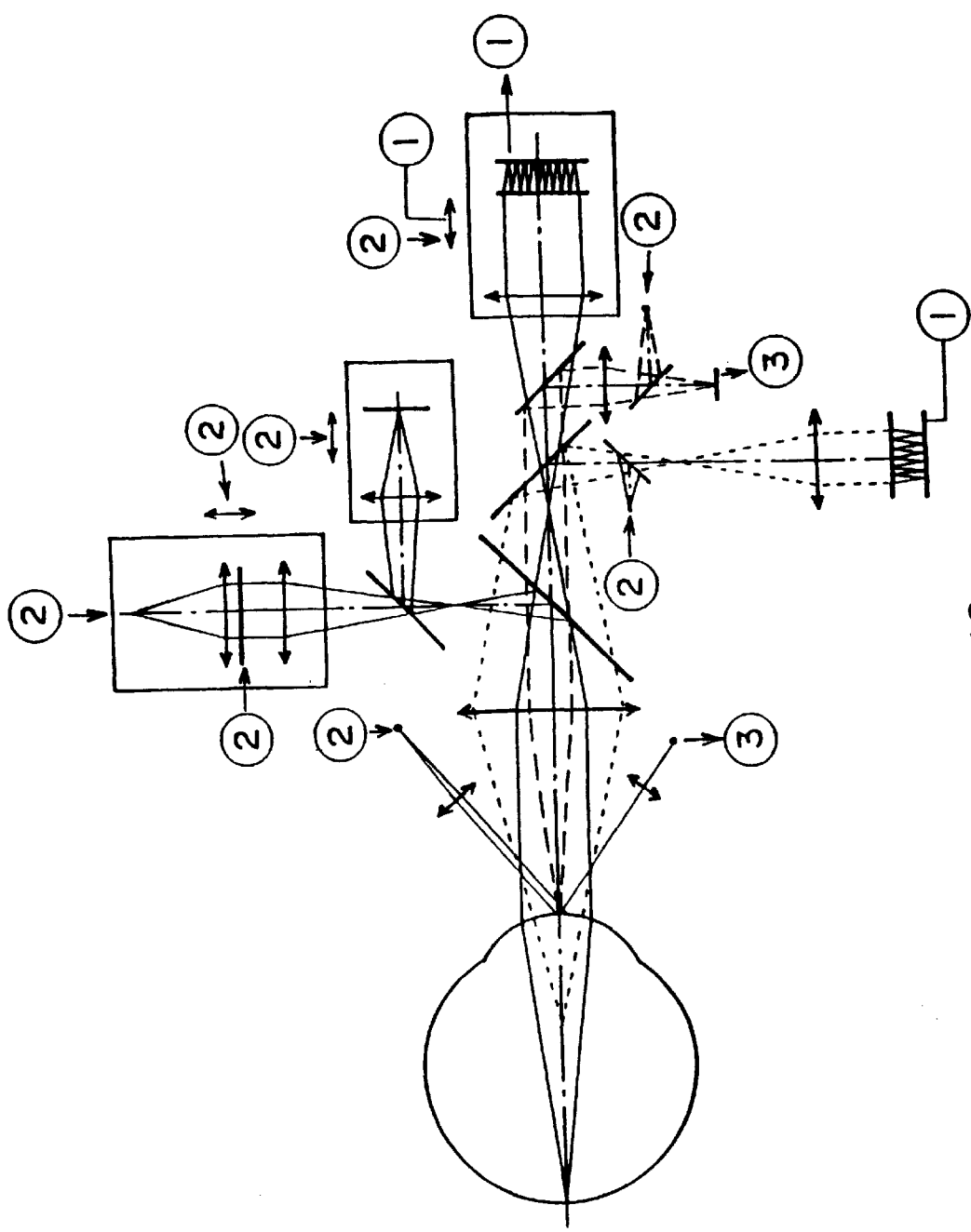
FIG. 12 is a block diagram showing the electrical configuration of the optical characteristic measuring apparatus 10000 in the fourth embodiment.
Figure 15A:
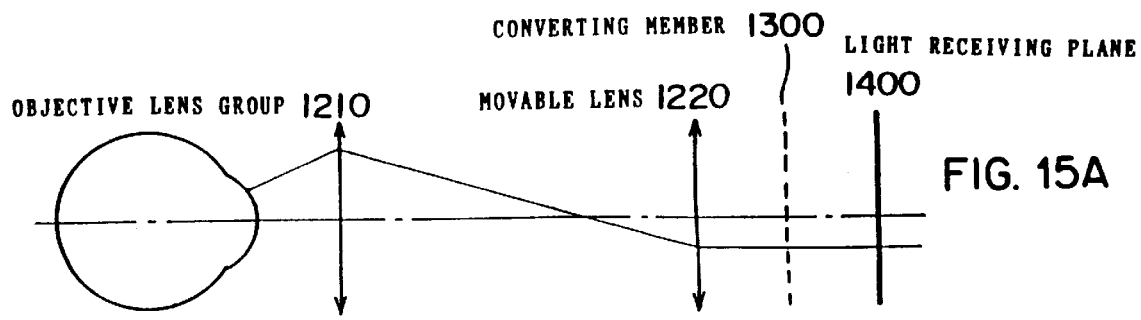
FIG. 15 is a diagrammatic view of assistance in explaining alignment.
Figure 15B:
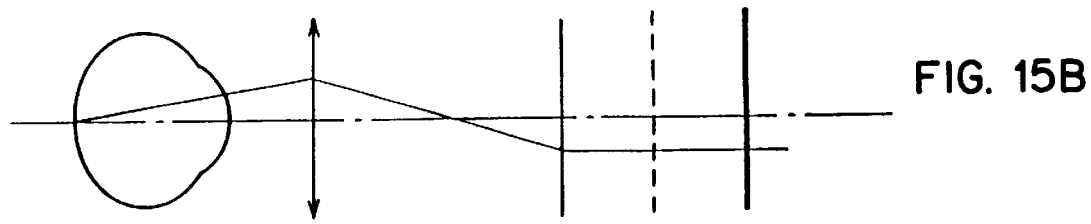
Figure 15C:
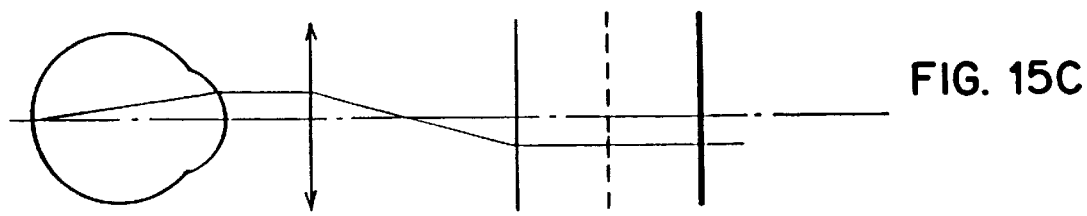
Figure 15D:
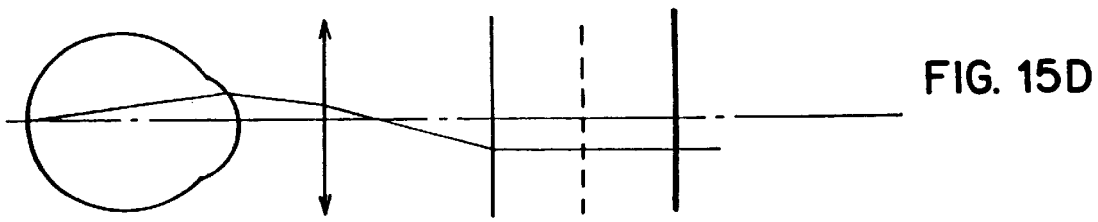

FIG. 12 illustrates the connection of the components of the optical characteristic measuring apparatus with electrical components.

The second illuminating optical system 2100 focuses light emitted by the second light source 2110 for illumination on a portion of the eye 1000 around the center of curvature of the cornea 1010 of the eye 1000.

The second illuminating optical system 2100 is used for illuminating the cornea 1010 entirely and hence does not need any diaphragm.

The second light source 2110 emits light of a second wavelength of 780 nm different from the first wavelength 840 nm of the light emitted by the first light source 1110.

The second wavelength of 780 nm is smaller than the first wavelength of 840 nm. Light of a wavelength outside the wavelength region of visible light is less offensive to the eye.

After completing alignment, which will be described later, the second illuminating optical system 2100 focuses light emitted by the second light source 2110 through a beam splitter 2120 on the center of curvature of the cornea 1010.

The second reflected light guiding optical system 2200 comprises an afocal lens 2210, and a second converting device 2300 which converts the reflected light rays into at least seventeen light beams.

The second reflected light guiding optical system 2200 guides the reflected light rays reflected from the cornea 1010 of the eye 1000 to the light receiving device. In a state where alignment is completed, the second light receiving device 2400 or the second converting device 2300 is substantially conjugate with the cornea 1010.

A fixation point optical system 3100 comprises a fixation point image forming lens 3110 and a fixation point 3120.

Light rays transmitted by the first illuminating optical system 1100 and light rays transmitted by the fixation point optical system 3100 are combined coaxially.

The fixation point optical system 3100 can be adjusted to show a pattern to the eye 1000, to blur an image or to fix the line of sight of the eye 1000. The fixation point optical system 3100 can be moved along its optical axis according to the refractive power of the eye 1000.

An XY alignment optical system 4100 comprises a third light source 4110, a lens 4120 and a two-dimensional imaging device 4130.

The XY alignment optical system 4100 makes a point source coincide with a point near the vertex of the cornea 1010.

The third light source 4110 emits light of 940 nm in wavelength.

The two-dimensional imaging device 4130 may be either a two-dimensional PSD (Position Sensing Detector) or a CCD. An image of a point source is formed at the center of the two-dimensional imaging device 4130.

A Z alignment optical system 5100 comprises a fourth light source 5110, a collimator lens 5120, a condenser lens 5130 and a linear imaging device 5140.

The Z alignment optical system 5100 makes a point source coincide with a point near the vertex of the cornea 1010.

The linear imaging device 5140 is a linear PSD, but may be an imaging device of any suitable type.

The Z alignment optical system 5100 collimates light rays emitted by the fourth light source 5110 and illuminates the cornea 1010 with parallel light rays. The linear imaging device 5140 is disposed at a point to receive light rays reflected by regular reflection on a plane including an illumination optical axis and a reflection optical axis.

The Z alignment optical system 5100 is disposed so that the parallel light rays intersects the optical axis of the collimator lens 5120 when positioned at a predetermined distance.

A first beam splitter 6100 is a semitransparent mirror, A second beam splitter 6200 is an optical element which reflects light of a wavelength around 780 nm entirely, and transmits light of a wavelength of a wavelength on the infrared side of 780 nm. A third beam splitter 6300 is a low-pass filter which transmits light of a wavelength around 840 nm and reflects light of a wavelength around 940 nm entirely.

The operation of the XY alignment optical system 4100 will be described with reference to FIG. 13.

The third light source 4110 is turned on instep S1.

The lens 4120 focuses light rays on the cornea 1010 in step S2. The position of a bright point is observed by the two-dimensional imaging device 4130 in step S3. Data is displayed on a monitor in step S4 if manual alignment is selected. Data is sent to the control unit in step S5 if automatic alignment is selected.

The operation of the Z alignment optical system 5100 will be described with reference to FIG. 14. The fourth light source 5110 is turned on in step S1. Light rays are collimated by the collimator lens 5120 and a portion of the eye 1000 around the vertex of the cornea 1010 is illuminated with parallel light rays in step S2. A virtual image is formed in step S3, and the virtual image is projected on the linear imaging device 5140 by the condenser lens 5130 in step S4. The linear imaging device 5140 provides measured data on the position of the virtual image in step S5 and sends the measured data on the position of the virtual image to the control unit in step S6.

Alignment will be described in detail with reference to FIG. 15.

Suppose that the lenses on the eye side of the movable lens of the reflected light guiding system form a objective lens group. Alignment can be achieved by disposing the objective lens group so that the front focal point of the objective lens group coincide with a reference measuring plane of a front portion of the eye 1000 (exit pupil, the surface of the cornea).

The movable lens moves so that the front focal point of the movable lens coincides with a point where the measuring light rays traveled through the objective lens group intersect the optical axis. (The point is substantially conjugate with the center of curvature of the cornea 1010 when the shape of the cornea 1010 is measured, and is substantially conjugate with the eyeground when the optical characteristics are measured.) Consequently, substantially parallel light rays fall always on the light receiving device and a measuring region on the reference measuring plane can be substantially fixed.

The accurate position of the light rays on the reference measuring plane of the front portion of the eye 1000 can be determined by measuring the coordinates of the light rays at a point conjugate with the reference measuring plane of the front portion of the eye 1000 after the movable lens on the basis of data on the position at which light rays fall on the light receiving device by interpolation or extrapolation, and dividing the coordinates of the light rays by the lateral magnification of the optical system.

FIGS. 15(a), 15(b), 15(c) and 15(d) illustrates a state for measuring the shape of the cornea 1010, a state for measuring the optical characteristics, a state for measuring emmetropia and a state for measuring myopia, respectively, in which the measuring region on the reference measuring plane is substantially fixed.

The first converting device 1300 will be described.

The first converting device 1300 included in the first reflected light guiding optical system 1200 is a wavefront converting member which converts the reflected light rays into a plurality of light beams. The first converting device 1300 has a plurality of micro Fresnel lenses arranged in a plane perpendicular to the optical axis thereof.

Micro Fresnel lenses will be described in detail.

A micro Fresnel lens is an optical element having annular bands at height pitches for wavelengths and an optimized blaze at a focal point. A micro Fresnel lens which can be applied to the present invention has, for example, eight levels of optical path differences produced by semiconductor fine processing techniques, and is capable of achieving focusing at a focusing efficiency of 98% when only primary light is used.

In the fourth embodiment, the first converting member 1300 is a wavefront converting device capable of converting the reflected light rays into at least seventeen light beams.

The second converting device 2300 is similar to the first converting device 1300 and hence the description thereof will be omitted.

The first light receiving device 1400 receives a plurality of light beams from the first converting device 1300. In the fourth embodiment, the light receiving device 1400 is a CCD. The CCD may be a common CCD for TV use or a CCD having 2000×2000 elements for measurement use.

Although a CCD for TV use as the first light receiving device 1400 has a low resolution, the CCD for TV use is inexpensive and its output can be easily given to a personal computer which is used generally for image processing. NTSC image signals provided by a CCD and its driver can be easily given to a personal computer through an NTSC image input port.

Although a CCD for measurement use having 2000(2000 elements is expensive, analog signals representing measured values can be given to a personal computer if a CCD for measurement use is employed.

Signals provided by a CCD can be converted into corresponding digital signals, and the digital signals may be given to a personal computer.

The first light receiving device 1400 is substantially conjugate with the first converting device 1300 and the iris 1020 of the eye 1000.

The first reflected light guiding optical system 1200 maintains the substantially conjugate relation between the first converting device 1300 and the iris 1020 and may be provided with an adjusting system for carrying out adjustment so that the reflected light rays from the eyeground fall in substantially parallel light rays on the light receiving device in a first light receiving state, and the reflected light rays from the cornea 1010 fall in substantially parallel light rays on the light receiving device in a second light receiving state.

The first beam splitter 6100 is inserted in the first reflected light guiding optical system 1200 to direct the light transmitted by the illuminating optical system 1100 toward the eye 1000, and to transmit the reflected light.

The second light receiving device 2400 is the same in configuration and actions as the first light receiving device 1400 and hence the description thereof will be omitted.

The principle of operations of the arithmetic unit 9100 for determining the optical characteristics of the eye 1000 on the basis of the inclination of light rays provided by the first light receiving device 1400 will be described in detail.

An algorithm will be described in detail.

As shown in FIG. 2, coordinate axes X and Y are set on the first converting device 1300, and coordinate axes x and y are set on the first light receiving device 1400. Then, a wave surface is expressed by a polar coordinate system or a rectangular coordinate system.

$$X = (X'/\beta) \quad (1)$$

$$Y = (Y'/\beta) \quad (2)$$

where $\beta$ is the lateral magnification of the optical system.

If the optical system does not cause aberration, the relation between wavefront aberrations $W(X, Y)$ and $W'(X', Y')$ is expressed by:

$$W\{(X'/\beta), (Y'/\beta)\} = W'(X', Y') \quad (3)$$

The following appropriate polynomial is given.

$f(X, Y, Z \ldots; A, B, C \ldots)$ where $X, Y, Z, \ldots$ are quantities determined by coordinates, and $A, B, C \ldots$ are parameters.

Expression of a wave surface by the polynomial f will be examined; that is, optimum parameters $(A, B, C, \ldots)$ are calculated.

From the Hartmann's measuring principle, $$\frac{\partial W(X', Y')}{\partial X'} = \frac{dx(X', Y')}{l} \quad (4)$$

$$\frac{\partial W(X', Y')}{\partial Y'} = \frac{dy(X', Y')}{l}$$

Practically, data represents an inclinations and hence the derivative of each wave surface is used for calculation. In the present invention, measured data represents the inclination of light rays. The inclination can be determined by directly differentiating the wave surface at the coordinates of a position.

The wavefront sensor measures a lateral residual from a reference.

It is known that the following relation holds good in FIG. 2, in which $l$ is the distance between the first converting device 1300 and the first light receiving device 1400. Values $dx(X, Y)$ and $dy(X, Y)$ are calculated for each element of the first converting device 1300, having a center point at X, Y, in which dx and dy are distances along the x-axis and the y-axis between a predetermined origin on the first light receiving device 1400, and a point on the first light receiving device 1400 where the light beam falls on the first light receiving device 1400.

An origin corresponding to one element of the first converting device 1300 is a point on the first light receiving device 1400 where the converted light rays can be measured when the wave surface is uniformly flat, i.e., both the spherical component and the astigmatism component representing the refractive characteristic of the eye are 0diopter, and there is no residual of irregular astigmatism.

Suppose that dx and dy are deviations of the light beam from the reference point. Then, $$dx(X_i, Y_j) = x_{ij} - x^0_{ij} \quad (5)$$

$$dy(X_i, Y_j) = y_{ij} - y^0_{ij} \quad (6)$$

An expression, (number of measured data)×2, can be obtained by substituting f into the expressions (5), (6), and necessary parameters can be obtained by method of least squares.

Although the constant term of f cannot be determined because an expression obtained by differentiating f is used, the determination of necessary parameters is sufficient for the present invention.

Concretely, the Zernike's polynomial, i.e., an orthogonal function properly representing aberration in terms of geometrical optics, may be used.

The general term of the Zernike's polynomial is expressed by:

$$-Z'_{res}(r, \theta) = R^{n-2m}(r) \left\{ \begin{array}{c} \sin \\ \cos \end{array} \right\} (n - 2m)\theta \quad (7)$$

SIN FOR $n - 2m > 0$

COS FOR $n - 2m \leq 0$ $$\therefore R^{n-2m}(r) = \sum_{i=0}^{m} (-1)^s \frac{(n-s)!}{s!(m-s)!(n-m-s)!} r^{n-2s}$$

More specifically, the Zernike's polynomial is expressed by the following expressions.

$Z_{00} = 1$ $Z_{10} = x$ $Z_{11} = y$ $Z_{20} = 2xy$ $Z_{21} = -1 + 2y^2 + 2x^2$ $Z_{22} = y^2 - x^2$ $Z_{30} = 3xy^2 - x^3$ $Z_{31} = -2x + 3xy^2 + 3x^3$ $Z_{32} = -2y + 3y^3 + 3x^2y$ $Z_{33} = y^3 - 3x^2y$ $Z_{40} = 4y^3x + 4x^3y$ $Z_{41} = -6xy + 8y^3x + 8x^3y$ $Z_{42} = 1 - 6y^2 - 6x^2 + 6y^4 + 12x^2y^2 + 6x^4$ $Z_{43} = -3y^2 + 3x^2 + 4y^4 - 4x^4$ $Z_{44} = y^4 - 6x^2y^2 + x^4$

Seventeen sample points (at least sixteen sample points on four rows along the x-axis and four columns along the Y-axis, and one sample point) or above are necessary when those expressions are combined by fourth degree.

Algorithm will be concretely described with reference to FIG. 16.

In step S1, sample data is produced on the basis of he data provided by the first light receiving device 1400. A defocus component and an inclination component are determined by method of least squares in step S2. The defocus component and the inclination component are subtracted from the sample data in step S3. In step S4, a reference Curvature is determined on the basis of D and the position of the movable lens. In step S5, A is determined by method of least squares. In step S6, a query is made to see if the shape of the cornea is being measured. If the response in step S6 is affirmative, the value of f is multiplied by ½ in step S7 because the light rays are reflected twice, and mapping is executed in step S8.

If the response in step S6 is negative, step S7 is skipped and step S8 is executed.

Fifth embodiment

Figure 17:
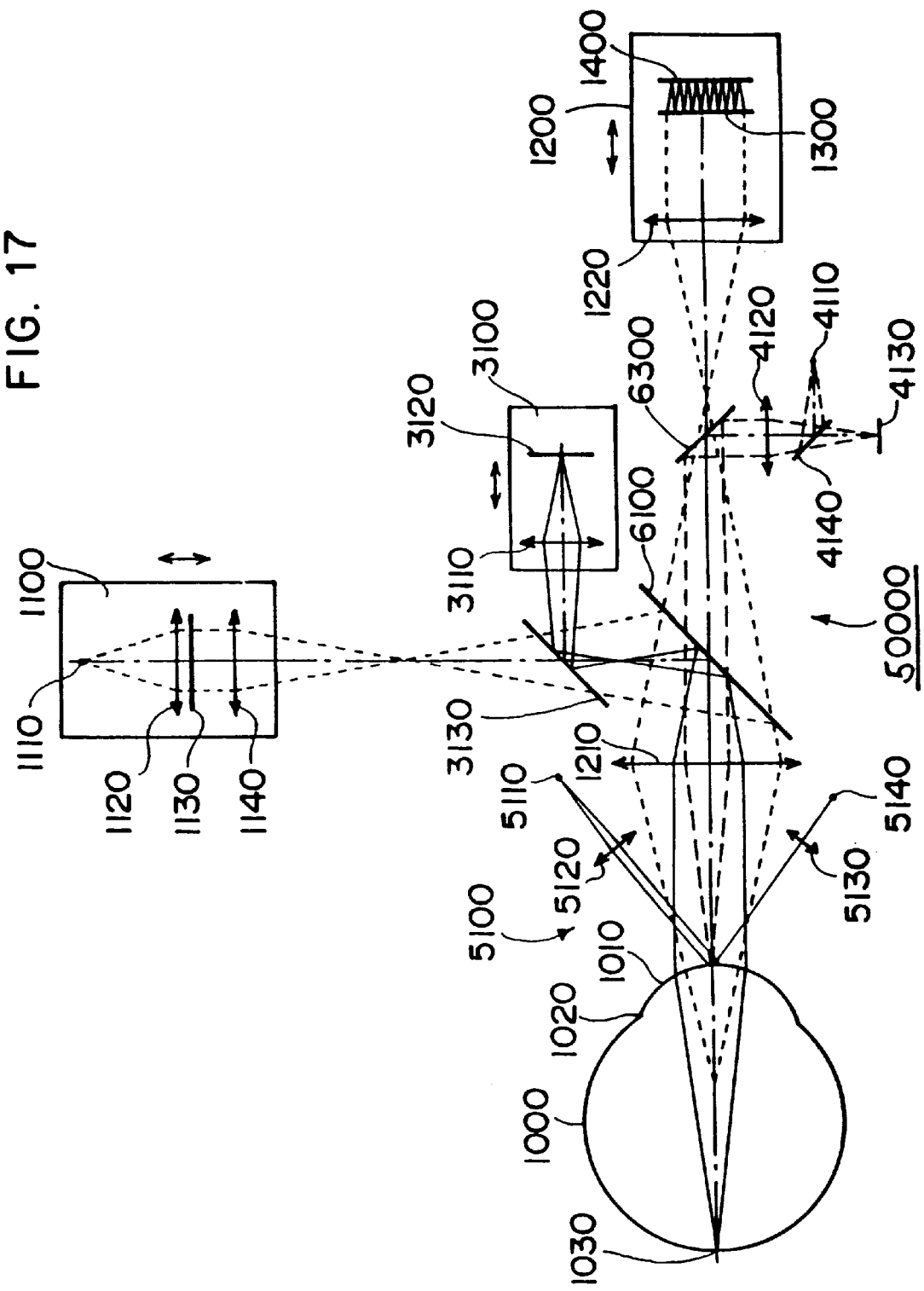
FIG. 17 is a diagrammatic view of an optical characteristic measuring apparatus in a fifth embodiment according to the present invention.
Figure 18:
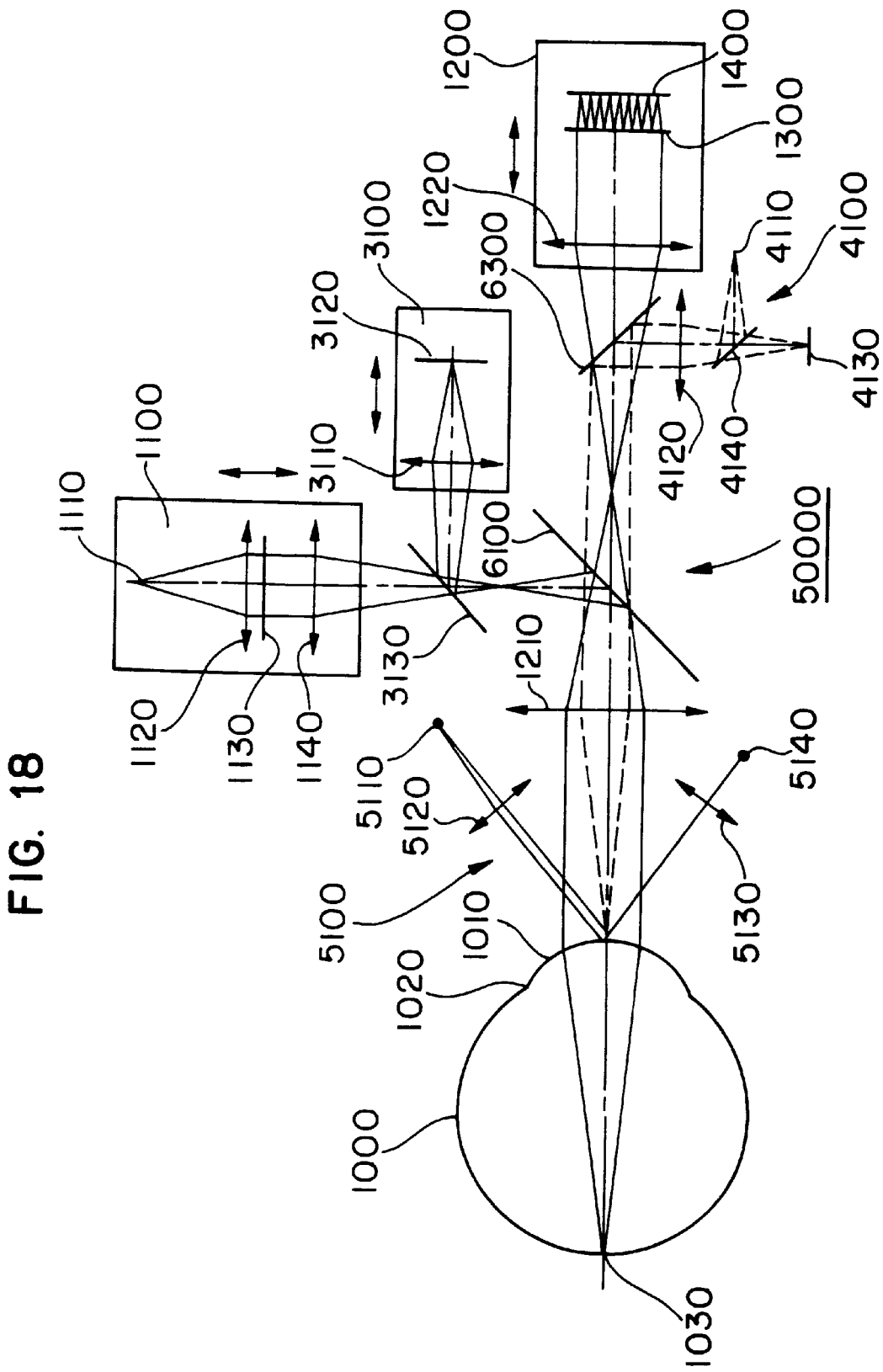
FIG. 18 is a diagrammatic view of the optical characteristic measuring apparatus in the fifth embodiment.

An optical characteristic measuring apparatus 50000 in a fifth embodiment according to the present invention for measuring the optical characteristics of the eye can be set for a first state for measuring the optical characteristics of the eye as shown in FIG. 17 or a second state for measuring the shape of the cornea as shown in FIG. 18, and is capable of carrying out measurement for both determining the optical characteristics of the eye and determining the shape of the cornea of the eye with common devices.

The optical characteristic measuring apparatus 50000 comprises a light source 1110, an illuminating optical system 1100 for illuminating a minute region in the eye with light rays emitted by the light source 1110, a reflected light guiding optical system 1200 for guiding light rays reflected from the eye to a light receiving device 1400, a converting device 1300 converting the reflected light rays into at least seventeen light beams and gives the light beams to the light receiving device 1400, and an arithmetic unit which determines the optical characteristics of the eye and the shape of the cornea of the eye on the basis of the inclination of light rays provided by the light receiving device 1400.

The illuminating optical system 1100 comprises a first condenser lens 1120, a light screening fiber 1130 and a second condenser lens 1140.

The illuminating optical system 1100 can be moved along its optical axis according to the refractive power of the eye in a distance range corresponding to a range of about −20 D to about +50 D so that light rays are focused on the eyeground of the eye. The illuminating optical system 1100 is moved to a position corresponding to +50 D for the measurement of the shape of the cornea.

The wavelength of light emitted by the light source 1110 may be that in the infrared region, such as 840 nm.

The light screening member 1130 sets different illuminating states respectively for the measurement of the eyeground the optical characteristics of the eyes measurement of the shape of the cornea.

The illuminating optical system 1100 can be moved according to the refractive power of the eye so that a first illuminating state is set to illuminate a minute region on the eyeground of the eye with light emitted by the light source 1110 to measure the eyeground the optical characteristics of the eyes or so that a second illuminating state is set to focus light emitted by the light source 1110 on a portion of the eye around the center of curvature of the cornea to measure the shape of the cornea.

When measuring the eyeground, an illuminating state 1A, in which the eye is illuminated through a portion thereof around the pupil, or an illuminating state 1B, in which the eye is illuminated through a portion thereof around the center of the pupil, is created.

When measuring the shape of the cornea, an ND filter is inserted in the optical path to create a second illuminating state to make the quantity of received light uniform because the reflectivity of the cornea is higher than that of the retina.

The light screening member 1130 may be a variable diaphragm provided with a first diaphragm having an aperture in its central portion, and a second diaphragm having an aperture in its peripheral portion.

When the first diaphragm of the variable diaphragm is inserted in the optical path, a region screened by the central screening portion is measured. When the second diaphragm of the variable diaphragm is inserted in the optical path, a region corresponding to a portion around the central aperture is measured.

The light screening member 1130 may be a liquid crystal device capable of forming an aperture in its central portion to set the illuminating state 1A and of forming an aperture in its peripheral portion to set the illuminating state 1B.

Accordingly, the light screening device 1130 is at a point substantially conjugate with the pupil of the eye, and is capable of creating the first illuminating state 1A for illumination through a region around the center of the pupil of the eye and the second illuminating state 1B for illumination through the periphery of the pupil of the eye.

The reflected light guiding optical system 1200 guides light rays reflected from the eye to the light receiving device. The reflected light guiding optical system 1200 comprises a first afocal lens 1210, a second afocal lens 1220, and a converting device 1300 for converting the reflected light rays into at least seventeen light beams.

The illuminating optical system 1100 guides the light rays to the light receiving device 1400 at a position substantially conjugate with the retina of the eye in a first light receiving state, and to guide the light rays to the light receiving device 1400 at a position substantially conjugate with the cornea of the eye in a second light receiving state.

Movement of the illuminating optical system 1100 and the reflected light guiding optical system 1200 is coordinated so that the positional relation between the illuminating optical system 1100 and the reflected light guiding optical system 1200 which makes a signal provided by the light receiving device 1400 when the reflected light rays reflected from a point on which the light rays emitted by the light source 1110 are focused fall thereon reach a peak is maintained. In the fifth embodiment, the illuminating optical system 1100 and the reflected light guiding optical system 1200 are moved in a distance range corresponding to a diopter range of −20 D to +50 D. Positions corresponding to about +50 D is used for the measurement of the shape of the cornea. Thus, the light rays emitted by the first light source 1110 is focused on the retina. The illuminating optical system 1100 and the reflected light guiding optical system 1200 are moved in directions to increase the peak of the output signal of the first light receiving device 1400 and are stopped at positions where the intensity of the light rays falling on the light receiving device 1400 is a maximum.

The reflected light guiding optical system 1200 can be moved along its optical axis according to the refractive power of the eye so that substantially parallel light rays fall on the converting device 1300.

Thus, in the fifth embodiment, the light receiving device 14 is used for both the measurement of the optical characteristics of the eye and the measurement of the shape of the cornea, so that the cost of the optical characteristic measuring apparatus is reduced.

The fifth embodiments are the same in other respects in constitution functions and operations as the first embodiment and hence the further description thereof will be omitted.

As is apparent from the foregoing description, the optical characteristic measuring apparatus of the present invention is capable of measuring the optical characteristics of the eye including irregular astigmatism and of measuring the shape of the cornea of the eye.

What is claimed is:

1. An optical characteristic measuring apparatus comprising:

a light source:

an illuminating optical system for illuminating a minute region on the retina of the eye with light rays emitted by the light source;

a light receiving device;

a reflected light guiding optical system for guiding reflected light rays reflected from the retina of the eye to the light receiving device;

a converting device capable of converting the reflected light rays into at least seventeen light beams and giving the light beams to the light receiving device; and an optical characteristic calculating unit for determining the optical characteristics of the eye on the basis of data provided by the light receiving device and representing an inclination of light rays.

2. An optical characteristic measuring apparatus comprising:

a light source:

an illuminating optical system for illuminating a minute region on the retina of the eye with light rays emitted by the light source;

a light receiving device;

a reflected light guiding optical system for guiding reflected light rays reflected from the retina of the eye to the light receiving device;

a converting device capable of converting the reflected light rays into at least seventeen light beams and giving the light beams to the light receiving device;

an optical characteristic calculating unit for determining the optical characteristics of the eye including a spherical component, a regular astigmatism component, the angle of the axis of the regular astigmatism component, and an irregular astigmatism component on the basis of data provided by the light receiving device and representing an inclination of light rays; and a display unit for displaying the optical characteristics of the eye including the spherical component, the regular astigmatism component, the angle of the axis of the regular astigmatism component, and the irregular astigmatism component.

3. The optical characteristic measuring apparatus according to claim 2, wherein the display unit is capable of graphically displaying the deviations of the optical characteristics of the eye from those of the normal eye or the optical characteristics including refractive power of the eye.

4. The optical characteristic measuring apparatus according to claim 1 or 2, wherein the converting device comprises a plurality of micro Fresnel lenses arranged in a plane perpendicular to its optical axis, and the optical characteristic calculating unit determines an inclination of reflected light rays from a position on the light receiving surface of the light receiving device on which the reflected light rays are converged, and determines the optical characteristics of the eye on the basis of the inclination.

5. The optical characteristic measuring apparatus according to claim 1, wherein the optical characteristic calculating unit discriminates between reflected light rays reflected from the retina and those reflected from the cornea on the basis of a mode of distribution of the reflected light rays on the light receiving device, and determines the optical characteristics of the eye on the basis of the inclination of the reflected light rays reflected from the retina.

6. The optical characteristic measuring apparatus according to claim 3, wherein the reflected light guiding optical system is constructed so that the light receiving device is dislocated slightly from a position conjugate with the eyeground of the eye or so that the converting device and the iris of the eye are in conjugate relationship.

7. The optical characteristic measuring apparatus according to claim 1 or 2, wherein the reflected light guiding optical system has an adjusting function to maintain the conjugate relationship between the converting device and the iris of the eye and to make the reflected light rays reflected from the eyeground substantially parallel light rays.

8. The optical characteristic measuring apparatus according to claim 1 or 2, wherein the illuminating optical system is adjusted according to the refractive power of the eye so as to illuminate a minute region on the eyeground of the eye with the light rays emitted by the light source.

9. The optical characteristic measuring apparatus according to claim 1 or 2, wherein the illuminating optical system is provided with a light screening member capable of creating a first illuminating state in which the eye is illuminated through a portion thereof around the center of the pupil, and a second illuminating state in which the eye is illuminated through a portion thereof around the pupil.

10. optical characteristic measuring apparatus according to claim 1 or 2, wherein the converting device is a liquid crystal device capable of forming a plurality of apertures.

11. The optical characteristic measuring apparatus according to claim 10, wherein the converting device is a liquid crystal device capable of forming a plurality of apertures at desired positions, and the optical characteristic calculating unit determines the optical characteristics of the eye accurately on the basis of inclinations of light rays traveled through the apertures formed respectively at different positions.

12. An optical characteristic measuring apparatus comprising:

a first light source which emits light rays of a first wavelength:

a first illuminating optical system for illuminating a minute region on the retina of the eye with light rays emitted by the first light source;

a first light receiving device;

a first reflected light guiding optical system for guiding reflected light rays reflected from the retina of the eye to the first light receiving device;

a first converting device capable of converting the reflected light rays reflected from the retina into at least seventeen light beams and giving the light beams to the first light receiving device;

a second Light source which emits light rays of a second wavelength different from the first wavelength;

a second illuminating optical system for illuminating a portion of the eye around the center of curvature of the cornea of the eye with light rays emitted by the second light source;

a second light receiving device;

a second reflected light guiding optical system for guiding reflected light rays reflected from the cornea of the eye to the second light receiving device;

a second converting device capable of converting the reflected light rays reflected from the cornea into at least seventeen light beams and giving the light beams to the second light receiving device; and an arithmetic unit for determining the optical characteristics of the eye on the basis of data provided by the first light receiving device and representing an inclination of light rays, and determining the shape of the cornea of the eye on the basis of data provided by the second light receiving device and representing an inclination of light rays.

13. The optical characteristic measuring apparatus according to claim 12 further comprising a display unit for displaying data provided by the arithmetic unit including the optical characteristics of the eye and the shape of the cornea.

14. The optical characteristic measuring apparatus according to claim 12 wherein the arithmetic unit estimates the optical characteristics of the eye from the shape of the cornea by calculation, compares the estimated optical characteristics with the optical characteristics determined on the basis of the output of the first light receiving device to decide abnormal optical characteristics due to factors other than the shape of the cornea.

15. The optical characteristic measuring apparatus according to claim 12, wherein the converting device comprises a plurality of micro Fresnel lenses arranged in a plane perpendicular to its optical axis, and the arithmetic unit determines the inclination of the reflected light rays from a position on the light receiving surface of the first light receiving device on which the reflected light rays are converted, and determines the optical characteristics of the eye on the basis of the inclination.

* * * * *

UNITED STATES PATENT AND TRADEMARK OFFICE
CERTIFICATE OF CORRECTION

PATENT NO. : 6,234,978 B1
DATED : May 22, 2001
INVENTOR(S) : Mihashi et al.

It is certified that error appears in the above-identified patent and that said Letters Patent is hereby corrected as shown below:

Title page,
Item [56], References Cited, U.S. PATENT DOCUMENTS,
"4,353,625  10/1982  Nohda" should read -- 4,353,625  10/1982 --
OTHER PUBLICATIONS, insert -- Patent Abstracts of Japan, vol. [?], No. [?], Aug. 16, 1994, JP 08 0625478 A (Fukugawa), Mar. 8, 1996. --

Column 6,
Line 20, "$(X^{2+Y^2}$" should read -- $(X^2+Y^2)$ --

Column 8,
Line 9, "r(n=2, 3, . . .)" should read -- $r^{2n}$ (n=2, 3, . . .) --
Line 12, "t" should read -- the --
Line 16, "deter" should read -- determined --
Line 19, "previouly" should read -- previously --
Line 26, "Pr" should read -- Fr --
Line 28, "approxiating" should read -- approximating --

Column 9,
Line 45, "are" should read -- is --

Column 11,
Line 4, "position s o n" should read -- positions on --
Line 19, "and. B." should read -- and B --

Column 14,
Line 45, "A" (second occurrence) should read -- a --
Line 55, "instep" should read -- in step --

Column 16,
Line 8, "2000(2000" should read -- 2000x2000 --

UNITED STATES PATENT AND TRADEMARK OFFICE
CERTIFICATE OF CORRECTION

PATENT NO. : 6,234,978 B1
DATED : May 22, 2001
INVENTOR(S) : Mihashi et al.

It is certified that error appears in the above-identified patent and that said Letters Patent is hereby corrected as shown below:

Column 17,
Line 30, "0diopter" should read -- 0 diopter --
Equation (5), "$dx(X_i, Y_j)-x_{ij}-x^o_{ij}$" should read -- $dx(X_i, Y_j)=x_{ij}-x^o_{ij}$ --
Equation (6), "$dy(X_i, Y_j)-y_{ij}-y^o_{ij}$" should read -- $dy(X_i, Y_j)=y_{ij}-y^o_{ij}$ --
Line 67, "$Z_{10}x$" should read -- $Z_{10}=x$ --

Column 18,
Line 10, "$3x_2y$" should read -- $3x^2y$ --
Line 20, "$6_x^2y^2+x^4$" should read -- $6x^2y^2+x^4$ --
Line 36, "SS" should read -- S5 --
Line 66, "fiber" should read -- member --

Signed and Sealed this

Tenth Day of September, 2002

Attest:

Attesting Officer

JAMES E. ROGAN
*Director of the United States Patent and Trademark Office*